(12) United States Patent
Garcia et al.

(10) Patent No.: US 6,486,202 B1
(45) Date of Patent: Nov. 26, 2002

(54) INHIBITORS OF ISOPRENYL TRANSFERASE

(75) Inventors: Ana Maria Garcia, Belmont, MA (US); James Kowalczyk, Andover, MA (US); Michael D. Lewis, Andover, MA (US)

(73) Assignee: Eisai Company, Limited, Tokyo (JP)

( * ) Notice: Subject to any disclaimer, the term of this patent is extended or adjusted under 35 U.S.C. 154(b) by 0 days.

(21) Appl. No.: 09/835,274

(22) Filed: Apr. 13, 2001

(51) Int. Cl.[7] .............. A61K 31/34; A61K 31/235; C07D 307/02
(52) U.S. Cl. .............. 514/471; 514/449; 514/542; 549/493; 560/22
(58) Field of Search .............. 549/493; 560/22; 514/449, 471, 542

(56) References Cited

U.S. PATENT DOCUMENTS

| 5,602,098 A | 2/1997 | Sebti et al. ............... 514/18 |
|---|---|---|
| 5,840,918 A | 11/1998 | Lewis et al. ............... 549/77 |
| 6,265,603 B1 | 7/2001 | Lewis et al. ............... 560/9 |

FOREIGN PATENT DOCUMENTS

| WO | WO 95/25086 | 9/1995 |
|---|---|---|
| WO | WO 95/34535 | 12/1995 |

OTHER PUBLICATIONS

Barbacid, M., Ann. Rev. Biochem., 56:779 (1987).
Bos, J.L., Cancer Res. 49:4682 (1989).
Cox, A.D., and Der, C.A. *Critical Rev. in Oncogenesis*, 3(4) 365–400 (1992).
Hancock, J.F. et al., *Cell* 57:1167 (1989).
Maltese, W.A. *FASEB Journal*, f:3319 (1990).
Moores et al., J. Biol. Chem., 266:14603 (1991).

*Primary Examiner*—Amelia Owens
(74) *Attorney, Agent, or Firm*—Hale and Dorr LLP

(57) ABSTRACT

Provided are novel peptidomimetic isoprenyl transferase inhibitors, methods for synthesizing such inhibitors, and methods for the use of such inhibitors for the treatment of tumors.

6 Claims, 1 Drawing Sheet

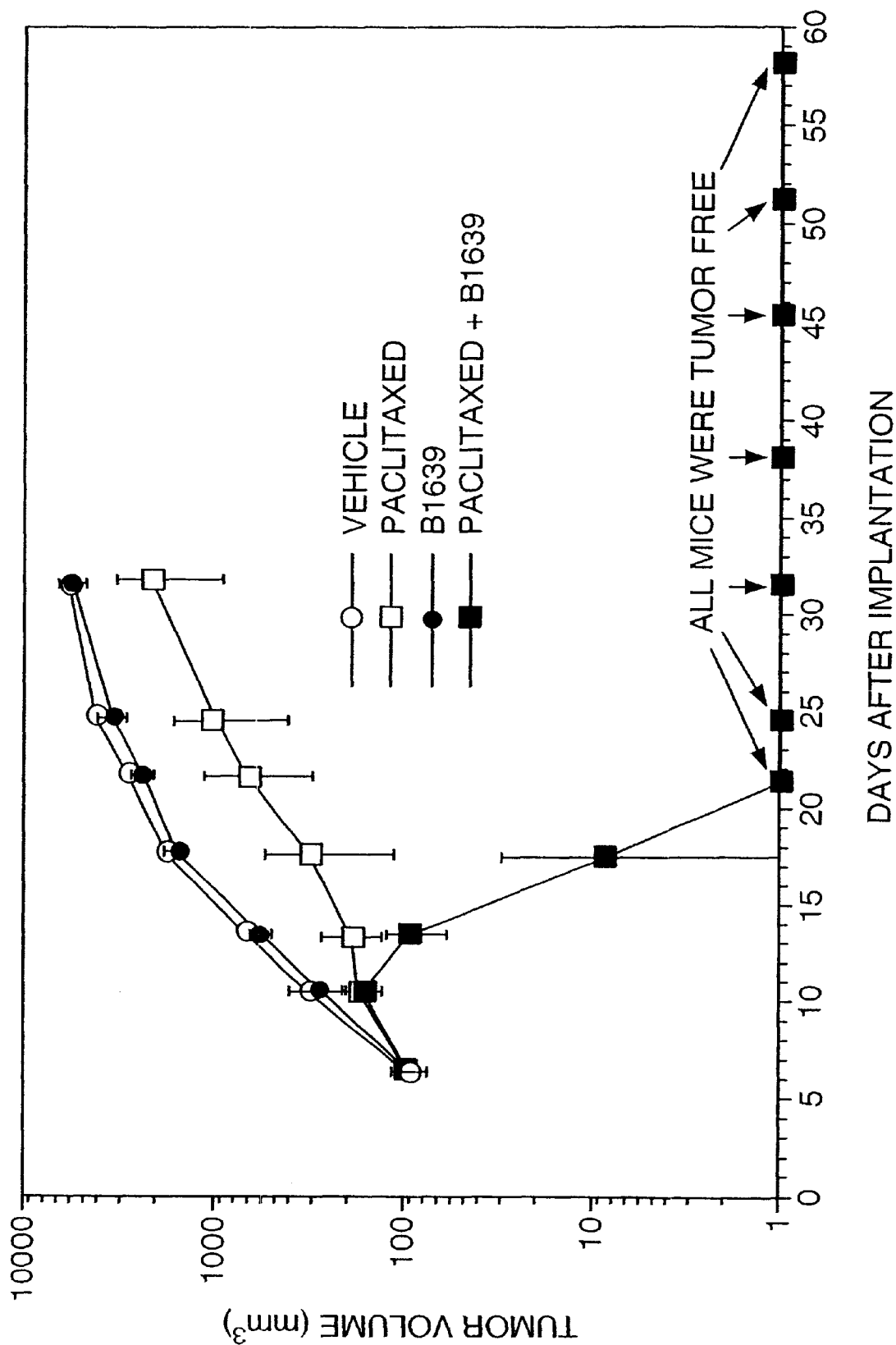

INHIBITORS OF ISOPRENYL TRANSFERASE

BACKGROUND OF THE INVENTION

This invention concerns peptidomimetic isoprenyl transferase inhibitor compounds useful in the treatment of human cancers.

Ras oncogenes are prevalent in over 20% of all human cancers. The compounds of the invention inhibit the post-translational processing of ras proteins, thereby inhibiting ras protein function.

Ras proteins are present in all cell types, and are thought to take part in normal cellular signal transduction mechanisms. Ras mutations are thought to cause hyperproliferation of cells; mutated ras genes are known as oncogenes. In particular, ras oncogenes are found in approximately 30% of all lung cancer, 30% of all myeloid leukemia, 50% of all colorectal carcinoma, and 90% of all pancreatic carcinoma. Barbacid, M., Ann. Rev. Biochem., 56:779 (1987), Bos, J. L., Cancer Res. 49:4682 (1989). Examples of ras mutations are found in H-ras, K-ras, and N-ras.

Like other members of the superfamily of small GTP-hydrolyzing proteins, ras-encoded proteins, both normal and mutated, require post-translational processing for cell membrane association and biological activity. Maltese, W. A., FASEB Journal, 4:3319 (1990), Hancock, J. F. et aL, Cell, 57:1167 (1989).

The post-translational processing of ras proteins is signaled by a short carboxyl-terminus consensus sequence, known as the CAAX box. This sequence signals which of two isoprenyl groups, farnesyl or geranylgeranyl, is to be attached to ras proteins by cellular enzymes. A farnesyl group is a 15 carbon isoprenyl group, while a geranylgeranyl group is a 20 carbon isoprenyl group. Isoprenyl groups are multimers of isoprene, a 5 carbon compound. For farnesylated proteins, such as ras, lamin B, and γ-transducin, C is cysteine, A is an aliphatic amino acid, and X (the carboxyl-terminal amino acid) is methionine, serine, or glutamine. Geranylgeranylated proteins such as Rap, Rho and other small GTP-binding proteins, have similar CAAX sequences in which X is usually leucine, or occasionally is phenylalanine. In vivo, ras proteins are preferentially farnesylated.

Post-translational processing of the ras-encoded protein includes at least three steps. First, reaction with farnesyl pyrophosphate attaches a farnesyl group to the Cys residue on the sulfhydryl side chain. Second, a specific protease cleaves the three carboxy-terminal amino acids. Third, the carboxylic acid moiety of the now-terminal cysteine is methylated to a methyl ester. The farnesyl transferase enzyme (FTase) mediates the attachment of the farnesyl group to a protein. The geranylgeranyl transferase I enzyme (GGTase I) mediates the attachment of the geranylgeranyl group to a protein.

Post-translational processing, particularly farnesylation, of ras proteins is critical for in vivo ras protein function. Among other things, farnesylation of ras oncogene products is known to be essential for ras-induced cellular transformation. Cox, A. D. and Der, C. A. Critical Rev. in Oncogenesis, 3 (4) 365–400 (1992). Upstream of FTase, farnesylation of a ras protein can be inhibited by mevalonate synthesis inhibitors such as lovastatin or compactin, which are HMG-CoA reductase inhibitors. Direct inhibition of FTase by short peptides or peptide-like substrates has also been demonstrated. Since ras proteins mediate the transformation of normal cells to cancer cells in many human cancers, compounds which inhibit prenylation will, therefore, inhibit the growth of ras-related cancers. A group of such compounds and methods for their synthesis are described in U.S. Pat. No. 5,840,918, the disclosure of which is incorporated by reference herein in its entirety, particularly the disclosure from column 17 to column 30, and Examples 1 to 175. Other compounds are disclosed in international patent publication WO 98/38162A1, which is also incorporated by reference herein in its entirety.

SUMMARY OF THE INVENTION

This invention is directed to novel peptidomimetic isoprenyl transferase inhibitor compounds useful in the treatment of ras-associated human cancers. Ras-associated human cancers are those in which a mutated form of the ras gene product are commonly found, e.g., lung cancers, myeloid leukemia, colorectal carcinoma, pancreatic carcinoma, and the like. In particular, the invention is directed to compounds with the following formulas:

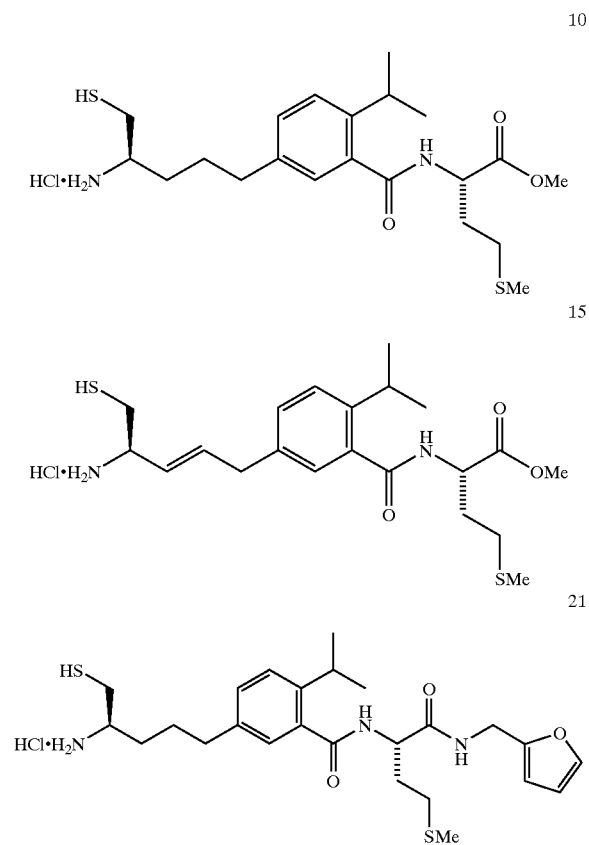

The invention concerns the compounds themselves, the preparation of these compounds, and the in vitro and in vivo isoprenyl transferase activity of these compounds. Another aspect of the invention is directed to the clinical use of the compounds to decrease isoprenyl transferase activity in biological systems, and to the physiological consequences of inhibition of isoprenyl transferase. In particular, the invention is directed to methods of using the compounds to treat ras-associated human cancers.

The compounds of the invention may be used clinically to treat medical conditions where a decrease in isoprenyl transferase activity is beneficial. The compounds of the invention can be used to inhibit post-translational modification of oncogenic ras proteins by FTase, thereby down-regulating ras protein-stimulated cell proliferation. Accordingly, the invention is directed to the treatment of various forms of ras-associated cancer. Some compounds of the invention inhibit post-translational modification of ras proteins by the related GGTase I, which also results in down-regulation of ras protein function. Certain compounds of the invention are selective or specific for FTase and are preferred over compounds which are selective for GGTase I.

Further, compounds of the present invention may contain asymmetric carbon atoms and hence can exist as stereoisomers, both enantiomers and diastereomers. All stereoisomers and mixtures thereof are considered to fall within the scope of the present invention. The synthetic examples cited herein provide the most preferred isomer.

The invention is also directed to prodrugs and pharmaceutically acceptable salts of the compounds described, and to pharmaceutical compositions suitable for different routes of drug administration and which comprise a therapeutically effective amount of a described compound admixed with a pharmacologically acceptable carrier.

The compounds of the invention have been found to be surprisingly and unexpectedly superior inhibitors of in vivo isoprenylation, i.e., isoprenylation of proteins, particularly ras proteins, when contacted with intact cells, compared with other known isoprenyltransferase inhibitor compounds. Without being bound by theory, it is believed that the increased lipophilicity of the compounds of the invention relative to other similar compounds provides for greater in vivo activity due to greater cell permeation.

Definitions

The term "prodrug" as used herein refers to any compound that may have less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein. The groups illustrated are exemplary, not exhaustive and one skilled in the art could prepare other known varieties of prodrugs. Such prodrugs of the compounds of the invention fall within the scope of the present invention.

The term "pharmaceutically acceptable salt" includes salts of the compounds of the invention derived from the combination of a compound of this invention and an organic or inorganic acid. The compounds of the invention are useful in both free base and salt form. In practice the use of salt form amounts to use of base form; both forms are within the scope of the present invention.

The terms "treatment" or "treating" include prophylactic or therapeutic administration of compounds of the invention, for the cure or amelioration of disease or symptoms associated with disease, and includes any benefits obtained or derived from the administration of the described compounds.

Further, compounds of the present invention may contain asymmetric carbon atoms and hence can exist as stereoisomers, both enantiomers and diastereomers. All stereoisomers and mixtures thereof are considered to fall within the scope of the present invention. The synthetic examples cited herein provide the most preferred isomer.

BRIEF DESCRIPTION OF THE DRAWING

FIG. 1 is a graph that shows the effects on solid tumors produced by paclitaxel, compound 10 of the invention, or a combination of compound 10 and paclitaxel.

DETAILED DESCRIPTION OF THE INVENTION

All patents, patent applications and references referred to in this specification are hereby incorporated by reference in their entirety. In case of a conflict between material incorporated by reference and the present specification, the present specification controls.

The invention is directed to compounds with formulas 10, 15, and 21, as set forth below, and methods for synthesizing and using such compounds.

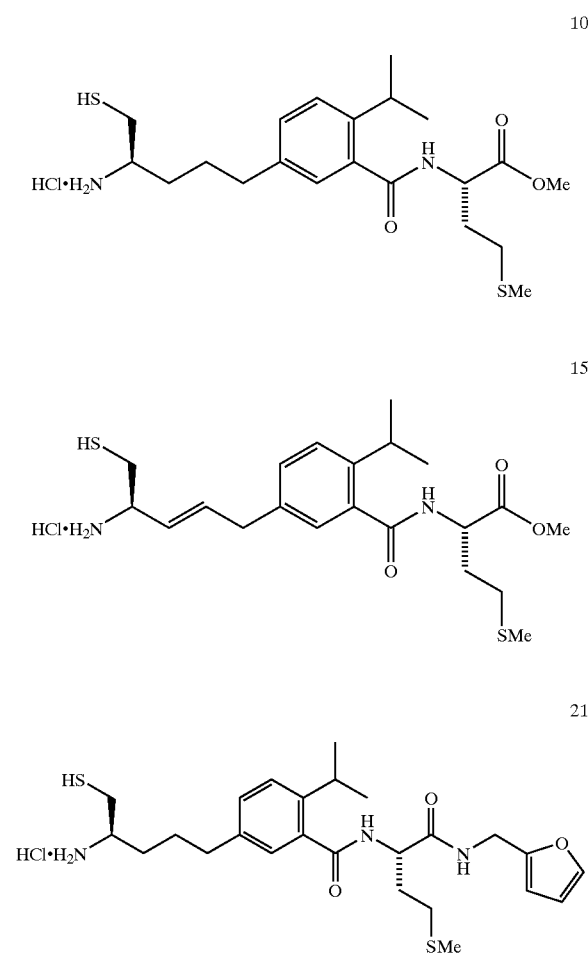

Preparation of the Compounds of the Invention

Schemes 1 to 6 are exemplary synthetic routes that have been used to make such compounds. These synthetic pathways can easily be modified by an organic chemist of ordinary skill to make the other, related compounds with similar properties.

Scheme 1
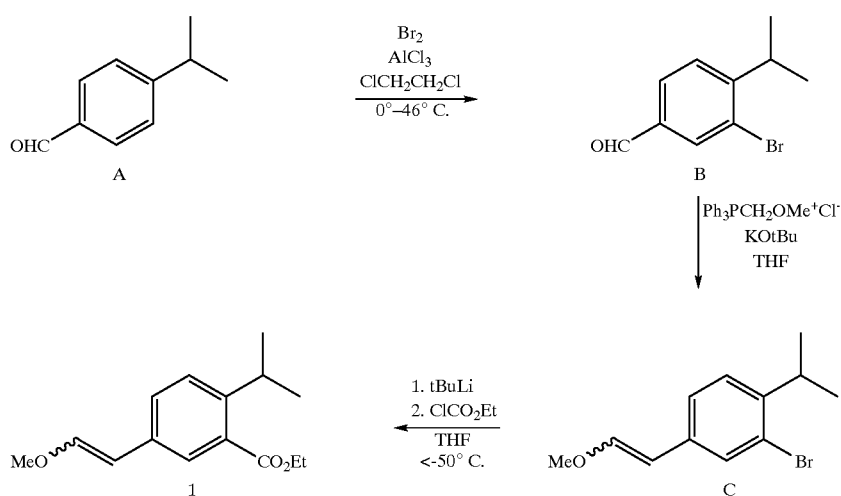
Scheme 2
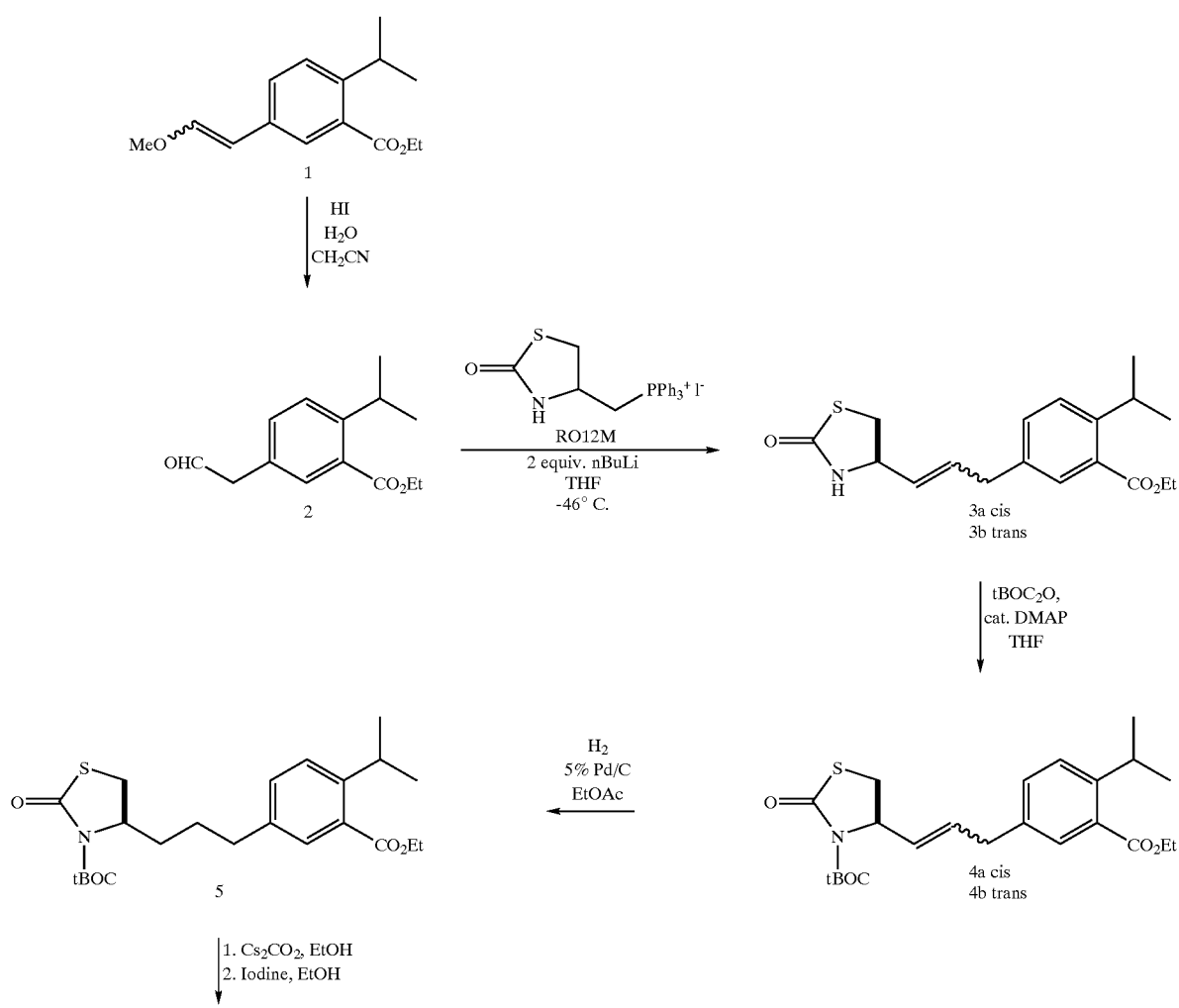

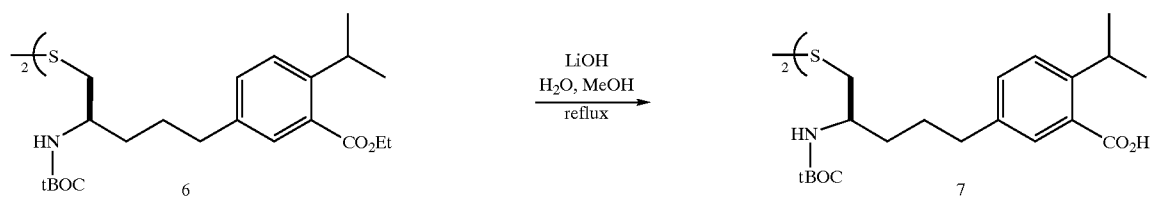
Scheme 2A
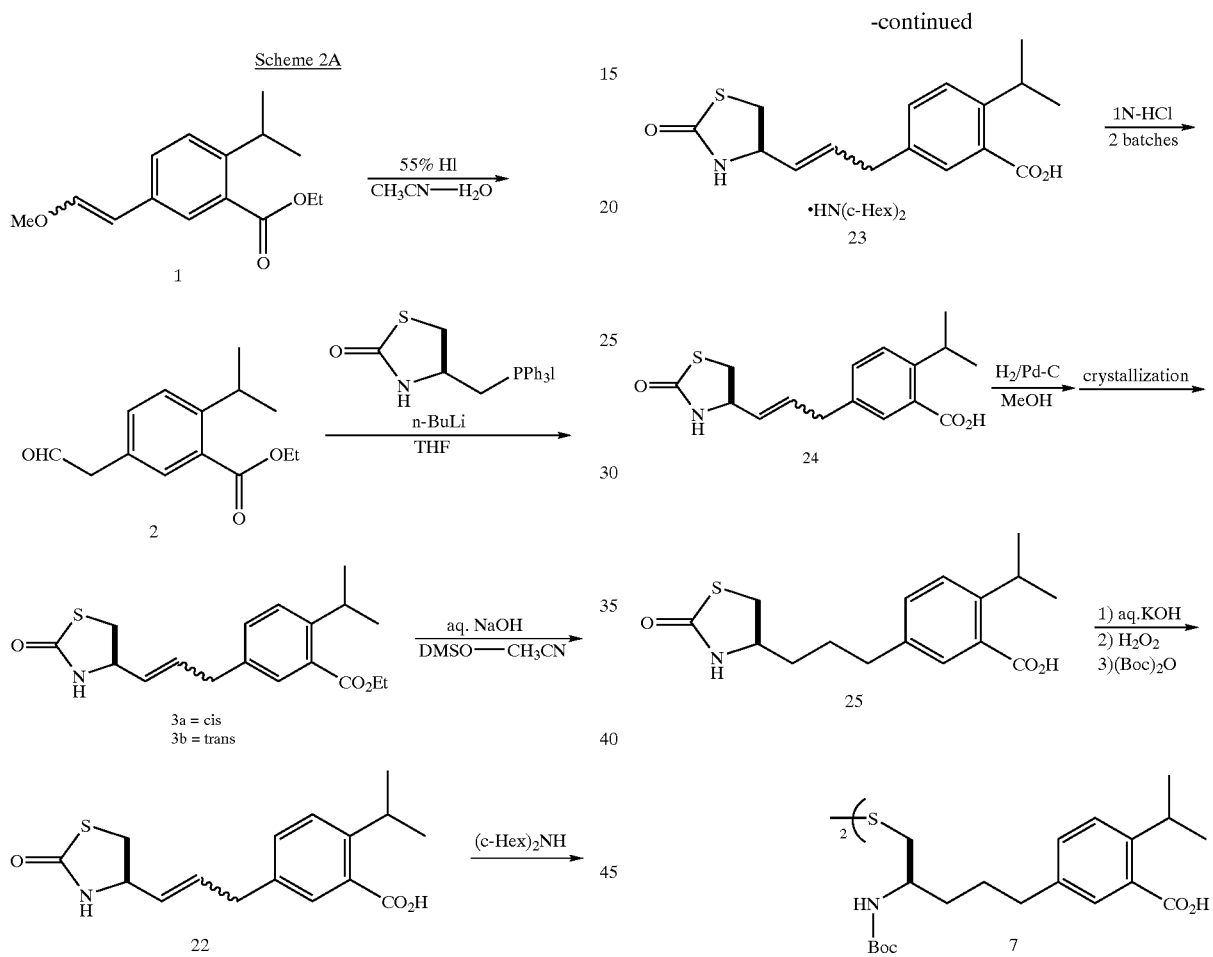
Scheme 3
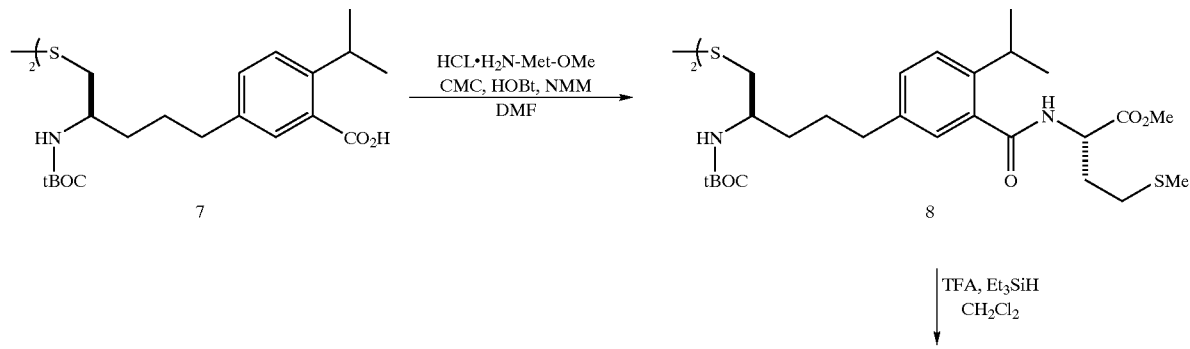

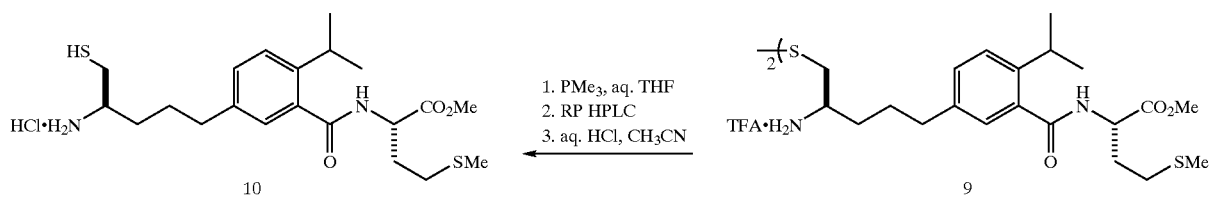
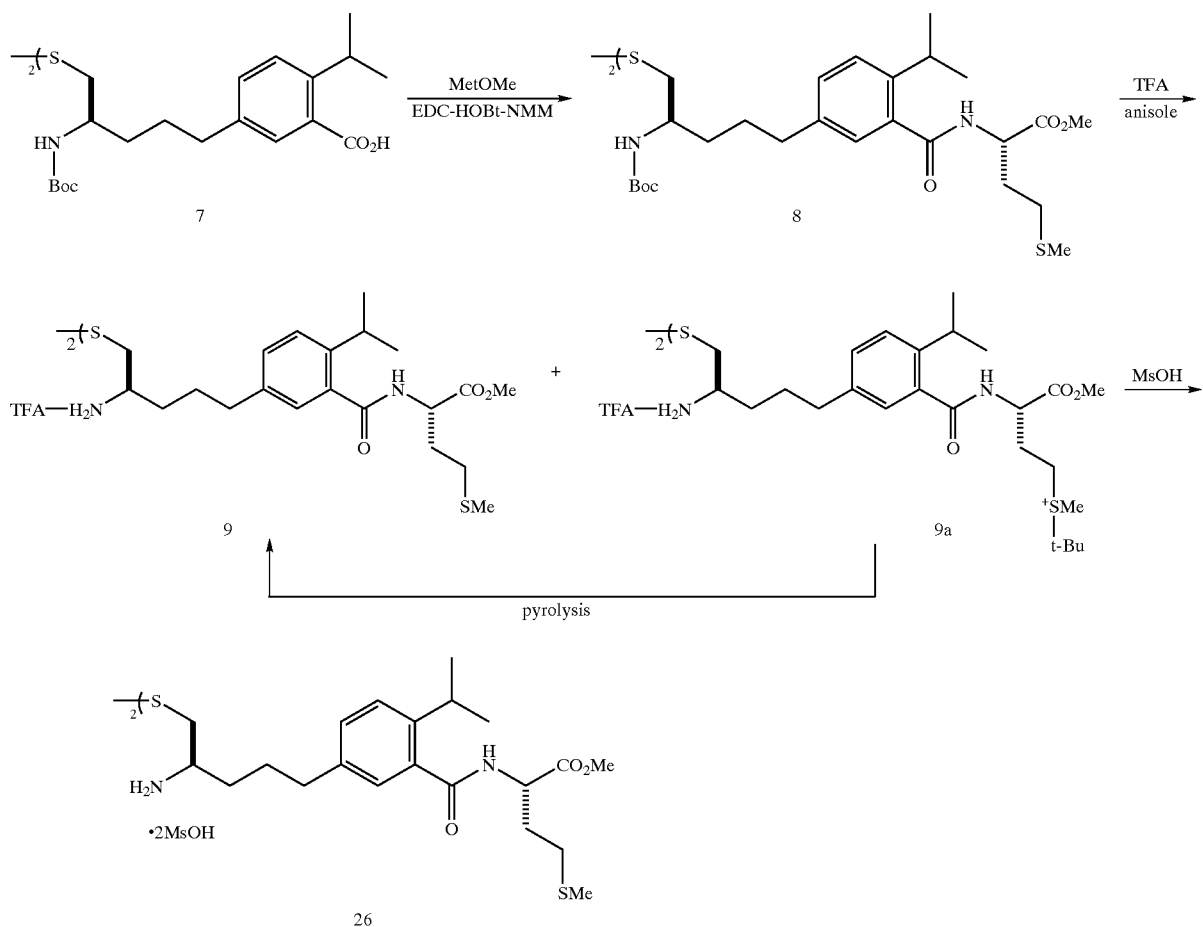
Scheme 3A
Scheme 4
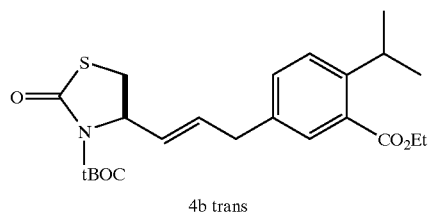

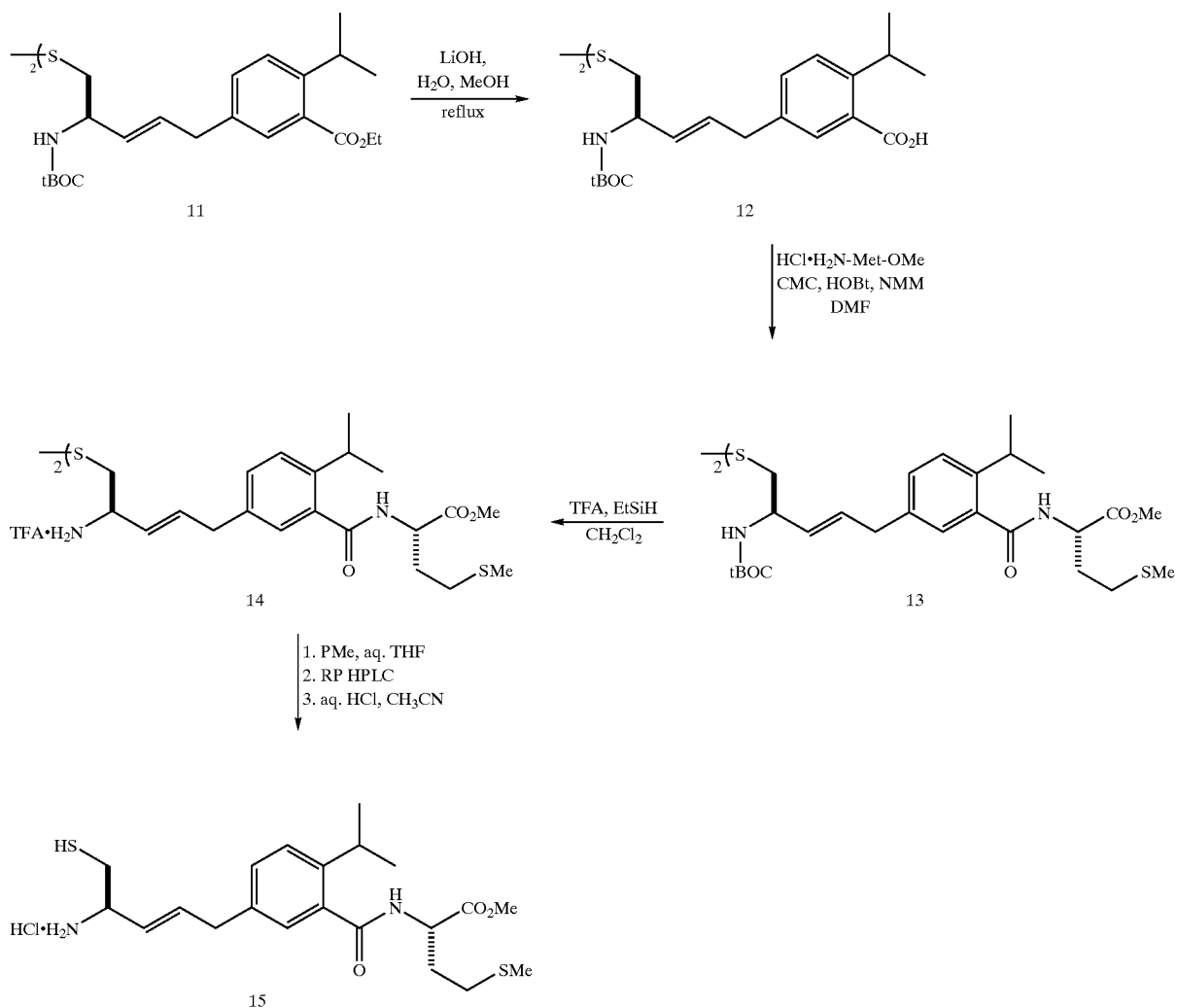
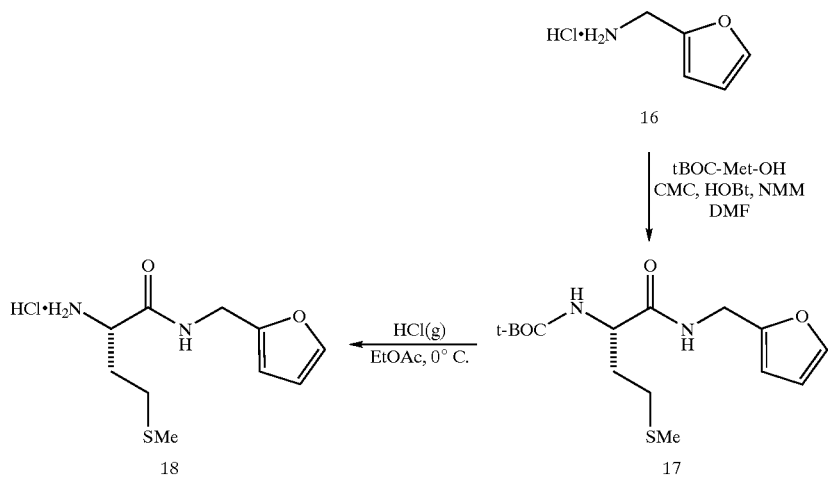
Scheme 5

Scheme 6

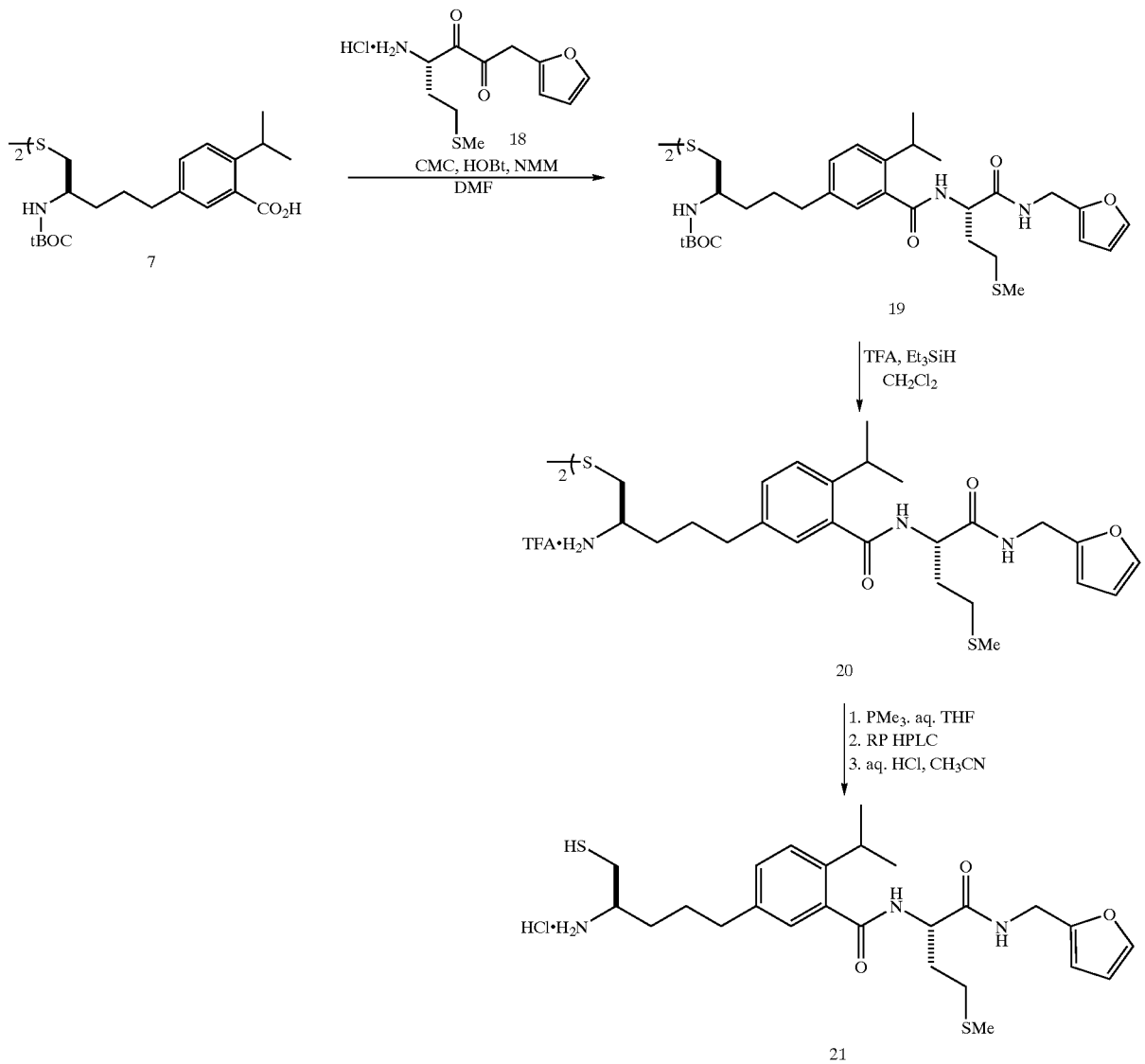

Formulations

Compounds of the present invention are administered to subjects in need of treatment in dosages which are effective to produce inhibition of isoprenyl transferases. Compound 10 can be administered, for example, by iv infusion of a solution or suspension with a concentration of between about 1 and 10 mg/mL. The total dose per subject per day should be between about 10 and 200 mg/m², preferably between about 25 and 150 mg/m², and more preferably between about 50 and 100 mg/m² of body surface area. A representative dosage regimen is daily administration for 5 days followed by 2 days rest. The administration cycle may be repeated every two weeks. Those of ordinary skill in the art will recognize that modification of dosage and administration routes can be made based on subject responsiveness to treatment.

An alternative method of administration is by way of infusion pump, at about a the concentration indicated above.

The term "parenteral" as used herein includes subcutaneous, intravenous, "intramuscular", and "intraarterial" injections with a variety of infusion techniques. Intraarterial and intravenous injection as used herein includes administration through catheters. Preferred for certain indications are methods of administration which allow rapid access to the tissue or organ being treated, such as intravenous injections for the treatment of cancer.

Pharmaceutical compositions containing the active ingredient may be in any form suitable for the intended method of administration.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e,g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl or n-propyl p-hydroxybenzoate.

The pharmaceutical compositions of the invention are preferably in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water, for injections, immediately prior to use. Extemporaneous injection solutions and suspensions may be prepared from sterile powders of the kind previously described.

It will be understood that the specific dosage form and dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

EXAMPLES

The compounds of this invention and their preparation can be understood further by the examples which illustrate some of the processes by which these compounds are prepared or used. Theses examples do not limit the invention. Variations of the invention, now known or further developed, are considered to fall within the scope of the present invention as hereinafter claimed.

Specific compounds of the present invention are referred to by compound number according to the tables below. In the synthetic procedures below, various liquid chromatography procedures were used to analyze purity. HPLC analysis was performed on SHIMADZU LC-10AT Liquid Chromatograph with SPD-10A UV detector and C-R7A plus chromatopac system. HPLC conditions were as follows:

| Method 1 | Column | Symmetry C18 (4.6 × 250 mm, Waters) |
|---|---|---|
| | Temp | r.t. |
| | Flow Rate | 1 mL/min |
| | Wave Length | 254 nm |
| | Eluent | MeOH/$H_2O$ = 850/150 |
| Method 2 | Column | Symmetry C18 (4.6 × 250 mm, Waters) |
| | Temp | r.t. |
| | Flow Rate | 1 mL/min |
| | Wave Length | 210 nm |
| | Eluent | $CH_3CN/H_2O$/70% $HClO_4$ = 550/450/1 |
| Method 3 | Column | Symmetry C18 (4.6 × 250 mm, Waters) |
| | Temp | r.t. |
| | Flow Rate | 0.6 mL/min |
| | Wave Length | 210 nm |
| | Eluent | $THF/H_2O/HClO_4$ = 400/600/1 |
| Method 4 | Column | Symmetry C18 (4.6 × 250 mm, Waters) |
| | Temp | r.t. |
| | Flow Rate | 1 mL/min |
| | Wave Length | 210 nm |
| | Eluent | $CH_3CN/H_2O$/70% $HClO_4$ = 400/600/1 |
| Method 5 | Column | Symmetry C18 (4.6 × 250 mm, Waters) |
| | Temp | r.t. |
| | Flow Rate | 1 mL/min |
| | Wave Length | 210 nm |
| | Eluent | $CH_3CN/H_2O$/70% $HClO_4$ = 700/300/1 |
| Method 6 | Column | Symmetry C18 (4.6 × 250 mm, Waters) |
| | Temp | r.t. |
| | Flow Rate | 1 mL/min |
| | Wave Length | 210 nm |
| | Eluent | $CH_3CN/H_2O$/70% $HClO_4$ = 800/200/1 |
| Method 7 | Column | YMC pro C18 (4.6 × 150 mm) |
| | Temp | r.t. |
| | Flow Rate | 1 ml/min |
| | Wave Length | 210 nm |
| | Eluent | $CH_3CN/H_2O$/70% $HClO_4$ = 800/200/1 |
| Method 8 | Column | YMC pro C18 (4.6 × 150 mm) |
| | Temp | r.t. |
| | Flow Rate | 1 mL/min |
| | Wave Length | 210 nm |
| | Eluent | $CH_3CN/H_2O$/70% $HClO_4$ = 450/550/1 |

EXAMPLE 1

Preparation of Compounds 10 and 26
3-Bromo-4-isopropylbenzaldehyde
(Compound B)

4-isopropylbenzaldehyde (A) (1200 g) was added dropwise over 86 minutes to an ice-bath cooled suspension of $AlCl_3$ (1296 g) in 4.8 L of dichloroethane in a 10 L, 4-necked flask equipped with a mechanical stirrer, a digital thermometer, a dropping funnel, and a gas outlet. The temperature of the mixture was maintained at approximately 6–14° C. during this period. The cooling bath was removed, and stirring was continued for an additional 1 hour at 13–14° C. The resulting wine-colored solution was warmed to 28° C., and bromine (1554 g) was added dropwise over 135 minutes, maintaining the internal temperature of 28–46° C. (bromine was introduced into the reaction solution directly via a Teflon extension tube). The generated HBr gas was evacuated via the gas outlet through an aqueous NaOH trap. The resulting dark solution was stirred at 35–42° C. for an additional 120 minutes while monitoring the progress by HPLC. Upon completion, the reaction mixture was cooled to room temperature and poured into a 20 L separatory apparatus containing 9 L of ice-water and 2 L of heptane. An additional 6 L of heptane was added, and the mixture was stirred mechanically. The organic layer was separated and washed with water (2 L), 2.5% aqueous $Na_2S_2O_3$ (4 L), water (2 L), 5% aqueous $NaHCO_3$ (4 L, a 10% aqueous NaCl (4 L) successively. The organic phase was dried over $MgSO_4$, (500 g), filtered, and concentrated under reduced pressure to give 2038 g (111%) of crude 3-bromo-4-isopropylbenzaldehyde as light brown oil. This material was used for the next step without further purification. A sample was distilled under vacuum to give the product as a light yellow (almost colorless) liquid. bp: 104–106° C. at 0.08 mmHg. The following values were obtained by nuclear magnetic resonance spectroscopy:

$^1$H NMR (CDCl$_3$) δ 9.88 (s 1H), 8.02 (d, J=1.6 Hz, 1H), 7.76 (dd, J=1.6 Hz, J=8.0 Hz, 1H), 7.42 (d, J=8.0 Hz, 1H), 3.34 (septet, J=6.8 Hz, 1H), and 1.25 (d, J=6.7 Hz, 6H).

1-Bromo-2-isopropyl-5-(2-methoxyvinyl)benzene (Compound C)

A 20-L, 4-necked flask equipped with mechanical stirrer, digital thermometer, and a N$_2$-inlet adapter was purged with nitrogen gas and charged with 1472 g of potassium tert-butoxide. THF (10 L) was added at room temperature, and the resulting solution was cooled in an ice-water bath. To this solution, methoxymethyl triphenylphosphonium chloride (4500 g) was added in portions over 20 minutes at approximately 2.5–14.6° C. The dark mixture was stirred for an additional 100 minutes at 0–12° C. 3-bromo-4-isopropylbenzaldehyde (compound B) (1988 g) dissolved in 1.5 L of THF was added to the reaction mixture via tubing over 85 minutes at 0–20° C. (followed by a 0.5 L THF rinse). HPLC analysis at 10 minutes after completion of addition showed complete conversion of starting material to desired products. The reaction was quenched by addition of 3 L of saturated aqueous NH$_4$Cl solution, and the mixture was divided into 2 portions. Each portion was poured into a 20 L separatory apparatus. 4.5 L of water and 4 L of toluene were added, and the mixture was stirred mechanically. The organic layer was separated and washed with 4 L of 10% aqueous NaCl. The combined organic extracts were concentrated under reduced pressure until triphenylphosphine oxide was precipitated. The concentrated mixture weighed 6000 g. An additional 6 L of heptane was added, and the mixture was stirred overnight at room temperature. The precipitate was filtered and washed with 4.5 L of heptane. The filtrate was concentrated under reduced pressure to give 2696 g (121%) of crude product as a dark oil. This material was combined with material (57 g) from another batch and distilled under vacuum (1.1 mmHg). Distillates in the range of 132–147° C. were collected to give 1869 g (82%, corrected for additional 57 g added) of 1-bromo-2-isopropyl-5-(2-methoxyvinyl) benzene (C) as a mixture of cis/trans isomers. The following values were obtained by nuclear magnetic resonance spectroscopy:

$^1$H NMR (CDCl$_3$) δ 7.76 (d, J=1.6 Hz), 7.41 (dd, J=1.6, 8.0 Hz), 7.39 (d, J=1.5 Hz), 7.10–7.17 (m), 7.00 (d, j=12.8 Hz, 1H, trans isomer), 6.12 (d, J=6.9 Hz, 1H, cis isomer), 5.70 (d, J=12.8 Hz, 1H, trans isomer), 5.12 (d, J=6.9 Hz, 1H, cis isomer), 3.79 (s, 3H, cis isomer), 3.68 (s, 3H, trans isomer), 3.32 (septet, J=6.8 Hz, 1H), and 1.24 (d, J=6.8 Hz, 6H).

Ethyl 2-isopropyl-5-(2-methoxyethenyl)benzoate (Compound 1)

tert-BuLi solution (1.7 M in pentane, 800 mL; 1.59 M in pentane, 2L; 4.5 mol total) was added via cannula over 135 minutes under nitrogen into a solution of 1-Bromo-6-isopropyl-3-(2-methoxyvinyl)benzene (C) (500 g, 1.96 mol) in anhydrous THF (3 L) at −50 to −75° C. The mixture was stirred for 1 hour after addition was complete. The solution was then transferred via cannula into a chilled (kept below −50° C.) solution of ethyl chloroformate (562 mL, 5.88 moles) in anhydrous THF (2 L), and the resultant solution was stirred for 68 minutes. The reaction was quenched by addition of 1 L of saturated aqueous NH$_4$Cl with stirring, followed by the addition of 2 L of water. The organic phase was separated, washed with a 10% NaCl solution. The solution was concentrated under vacuum to approximately. Evaporation furnished the crude product as a light yellow or greenish yellow liquid. A total of 3 batches were produced according to the above procedures, and 1.7 kg of crude product was obtained. The crude liquid product was distilled under high vacuum (0.9 mm Hg) and distillates in the range of 158 to 165° C. were collected to obtain 1075 g (yield 73%) of product. The following values were obtained by nuclear magnetic resonance spectroscopy:

$^1$H NMR (CDCl$_3$) δ 7.80 (d, J=1.8 Hz), 7.68 (dd, J=1.8, 8.1 Hz), 7.52 (d, J=1.3 Hz), 7.26–7.30 (m), 7.04 (d, J=12.9 Hz, 1H, trans isomer), 6.13 (d, J=7.0 Hz, 1H, cis isomer), 5.78 (d, J=12.9 Hz, 1H, trans isomer), 5.20 (d,)=7.0 Hz, 1H, cis isomer), 4.36 (q, J=7.1 Hz, 2H), 4.35 (q, J=7.0 Hz, 2H), 3.79 (s, 3H, cis isomer), 3.69 (s, 3H, trans isomer), 3.59–3.68 (m, 1H), 1.42 (t, J=7.1 Hz, 3H), 1.41 (t, J=7.1 Hz, 3H), and 1.26 (d, J=6.8 Hz, 6H).

Preparation of Ethyl 2-isopropyl-5-(formylmethyl)benzoate (Compound 2)

Compound 1 (25.62 g, 103.2 mmol) was dissolved in CH$_3$CN (370 mL) at room temperature under nitrogen. H$_2$O (15.5 mL) and a 57% aqueous solution of HI (14.7 mL) were added. The reaction solution was stirred at room temperature for 1 hour, and then was diluted with EtOAc (1000 mL), washed with H$_2$O (400 mL), 0.25N Na$_2$S$_2$O$_3$ (400 mL), H$_2$O (400 mL), and saturated aqueous NaCl (400 mL), dried over Na$_2$SO$_4$, filtered, evaporated, and dried under vacuum to afford 24.31 g (100%) of Compound 2 as a yellow oil, which was used without further purification. The following values were obtained by nuclear magnetic resonance spectroscopy:

$^1$H NMR (CDCl$_3$) δ 9.75 (t, J=2.3 Hz, 1H), 7.56 (d, J=1.8 Hz, 1H), 7.40 (d, J=8.2 Hz, 1H), 7.30 (dd, J=2.1 Hz, J=8.0 Hz, 1H), 4.36 (q, J=7.3 Hz, 2H), 3.69 (d, J=23 Hz, 2H), 3.68 (septet, J=6.9 Hz, 1H), 1.39 (t, J=7.1 Hz, 3H), and 1.25 (d, J=6.9 Hz, 6H).

Preparation of Methyl 2-isopropyl-5-{(E,Z)-3-[(4S)-2-oxo-1,3-thiazolan-4-yl]-2-propenyl}benzoate (Compounds 3a,3b)

A flask was charged with dry phosphonium salt RO12M (52.62 g, 104.1 mmol), and THF (500 mL) was added under nitrogen. The suspension was cooled to approximately −46° C. using a dry ice/acetone bath. nBuLi (2.5M in hexanes, 93.6 mL) was added drop-wise via an addition funnel over 16 minutes. The resulting deep red, homogeneous solution was stirred for 20 minutes. A solution of compound 2 (24.18 g, 103.2 mmol) in THF (50 mL) was added rapidly to the reaction solution via addition funnel, and the funnel was rinsed with THF (2×50 mL). The reaction mixture was stirred for 10 minutes, and then the cooling bath was removed. The solution was allowed to warm to room temperature over 40 minutes. The reaction was quenched at room temperature with saturated aqueous NH$_4$Cl and diluted with EtOAc (1500 mL) and H$_2$O (700 mL). The organic phase was separated, washed with pH 7.2 phosphate buffer (700 mL), H$_2$O (700 mL), and saturated aqueous NaCl (700 mL), dried over MgSO$_4$, filtered, and concentrated to give a reddish oil. Purification by flash chromatography (EtOAc/hexanes) furnished 22.5 g (65%) of Compound 3 (cis/trans mixture) as a pale yellow oil.

The following values were obtained by nuclear magnetic resonance spectroscopy:

3 cis: $^1$H NMR (CDCl$_3$) δ 7.47 (d, J=1.8 Hz, 1H), 7.34 (d, J=8.2 Hz, 1H), 7.23 (dd, J=2.1 Hz, 8.0 Hz, 1H), 5.83 (m, 1H), 5.65 (m, 1H), 5.45 (br s, 1H), 4.82 (q, J=2.1 Hz, 1H), 4.36 (q, J=6.9 Hz, 2H), 3.64 (septet, J=6.9, 1H), and 3.46 (m, 1H), 3.42 (d, J=7.3 Hz, 2H), 3.23 (dd, J=8.7 Hz, 11.0 Hz, 1H), 1.40 (t, J=7.1, 3H), 1.24 (d, J=6.6 Hz, 6H).

3 trans: $^1$H NMR(CDCl$_3$) δ 7.47 (d, J=1.8 Hz, 1H), 7.34 (d, J=7.8 Hz, 1H), 7.24 (dd, J=2.1 Hz, 8.0 Hz, 1H), 5.89 (m, 1H), 5.56 (m, 1H), 5.53 (br s, 1H), 4.36 (q, J=7.1 Hz, 2H), 3.63 (septet, J=6.9, 1H), and 3.47 (dd, J=7.3 Hz, J=11.0 Hz, 1H), 3.37 (d, J=6.9 Hz, 2H), 3.19 (dd, J=7.3 Hz, 3.7 Hz, 1H), 1.39 (t, J=7.1, 3H), 1.24 (d, J=6.9 Hz, 6H).

Preparation of Compound 4

Compound 3 (9–7415 g, 29.22 mmol) was dissolved in THF (185 mL), and (tBOC)$_2$O (11.54 g, 52.88 mmol) and DMAP (0.5136 g, 4.204 mmol) were added. The solution was stirred at room temperature for 2 hrs. The solution was diluted with EtOAc (800 mL), washed with H$_2$O (2×400 mL) and saturated NaCl (400 mL). The EtOAc layer was dried over NaSO$_4$, filtered and concentrated to afford a yellow oil that was purified by flash chromatography (eluting with EtOAc/hexanes) to furnish 11.1329 g (88%) of Compound 4 (cis/trans mixture) as a yellow oil.

The following values were obtained by nuclear magnetic resonance spectroscopy:

4 cis: $_1$H NMR (CDCl$_3$) δ 7.5 (d, J=1.8 Hz, 1H), 7.30 (d, J=8.2 Hz, 1H), 7.27 (dd, J=1.8 Hz, 8.2 Hz, 1H), 5.86 (m, 1H), 5.78 (m, 1H), 5.33 (m, 1H), 4.35 (q, J=7.3 Hz, 2H), 3.62 (septet, J=6.9 Hz, 1H), 3.60 (dd, J=7.3 Hz, 11.0 Hz, 1H), and 3.53 (d, J=7.3 Hz 2H), 2.85 (dd, J=2.3 Hz, 11.0 Hz, 1H), 1.50 (s, 9H), 1.38 (t, J=7.1 Hz, 3H), 1.23 (d, J=6.9 Hz, 6H).

4 trans: $^1$H NMR (CDCl$_3$) δ 7.49 (d, J=1.8 Hz, 1H), 7.32 (d, J=7.8 Hz, 1H), 7.25 (dd, J=1.8 Hz, 8.2 Hz, 1H), 5.87 (m, 1H), 5.75 (m, 1H), 4.93 (t, J=7.3 Hz, 1H), 4.35 (q,J=7.3 Hz, 2H), 4.36 Hz (q, J=7.3 Hz, H), 3.64 (septet, J=6.9 Hz, 1H), 3.61 (dd, J=6.6 Hz, 13.5 Hz, 1H), and 3.38 (d, J=16.9 Hz, 2H), 2.91 (dd, J=0.9 Hz, 11.0 Hz, 1H), 1.40 (s, 9H), 1.39 (t, J=7.1 Hz, 3H), 1.24 (dd, J=23 Hz, 6.9 Hz, 6H).

Preparation of Compound 5

A Parr apparatus was charged with a solution of Compound 4 (16.5031 g, 38.07 mmol) in EtOAc (250 mL), and 5% Pd/C catalyst (15.13 g) was added. The suspension was shaken under 50 psi H$_2$ overnight (17.5 hours). The mixture was filtered through Celite® and concentrated to give a black oil. This material was redissolved in EtOAc (250 mL) and placed in the Parr apparatus once again. Additional 5% Pd/C catalyst (15.69 g) was added. The mixture was shaken under 50 psi H$_2$ for about 5 hours. The mixture was filtered through Celite® and rinsed with EtOAc until the filtrate ran clear, and the filtrate was concentrated to give a black oil. Purification by flash chromatography (EtOAc/hexanes) gave 14.79 g (89%) of Compound 5 as a light yellow oil. The following values were obtained by nuclear magnetic resonance spectroscopy:

$^1$H NMR (CDCl$_3$) δ 7.49 (d, J=2.3 Hz, 1H), 7.30 (d, J=7.8 Hz, 1H), 7.25 (dd, J=1.8 Hz, 7.8 Hz, 1H), 4.43 (m, 1H), 4.36 (q, J=7.3 Hz, 2H), 3.63 (septet, J=6.9 Hz, 1H), 3.50 (dd, J=7.3 Hz, 11.0 Hz, 1H), and 2.86 (dd, J=11.0 Hz, 11.9 Hz, 1H), 2.66 (m, 2H), 1.40 (s, 9H), 1.63–1.96 (m, 4H), 1.45 (s, 9H), 1.39 (t, J=7.1 Hz, 3H), 1.23 (d, J=6.9 Hz, 6H).

Preparation of Compound 6

Compound 5 (19.9489 g, 45.80 mmol) was dissolved in EtOH (200 proof, 560 mL). Cs$_2$CO$_3$ (15.67 g, 48.17 mmol) was added, and the suspension was stirred at room temperature overnight (18 hours). Iodine (2.93 g, 23.09 mmol) was added to the homogeneous solution. The mixture was stirred at room temperature until the iodine dissolved (45 minutes). The solution was diluted with EtOAc (600 mL) and washed with 0.1 N HCl (500 mL), 0.25 N Na$_2$S$_2$O$_3$ (500 mL), H$_2$O (500 mL) and saturated aqueous NaCl (500 mL). The combined aqueous phases were back-extracted with EtOAc (600 mL). The combined organic phases were dried over MgSO$_4$, filtered, and concentrated to give a yellow oil. Purification by flash chromatography (EtOAc/hexanes) furnished 11.45 g (61%) of Compound 6 as a pale yellow oil. The following values were obtained by nuclear magnetic resonance spectroscopy:

$^1$H NMR (CDCl$_3$) δ 7.48 (d, J=1.8 Hz, 1H), 7.30 (d, J=8.2 Hz, 1H), 7.24 (d, J=1.8 Hz, 1H), 4.87 (br s, 1H), 4.35 (q, J=7.3 Hz, 2H), 3.87 (br s, 1H), 3.62 (septet, J=6.9 Hz, 1H), 2.94 (br s, 1H), and 2.80 (dd, J=5.5 Hz, 13.7 Hz, 1H), 2.55–2.66 (m, 2H), 1.60–1.80 (m, 4H), 1.43 (s, 9H), 1.38 (t, J=7.1 Hz, 3H), 1.22 (d, J=6.9 Hz, 6H).

Preparation of 5-((4S)-4-[(tert-butoxycarbonyl)amino]-5-{[(2S)-2-[(tert-butoxycarbonyl)amino]-5-(3-carboxy-4-isopropylphenyl) pentyl]-disulfanyl}pentyl)-2-isopropylbenzoic acid (Compound 7)

Compound 6 (4.34 g, 5.31 mmol) was dissolved in MeOH (100 mL), and LiOH (3.75 g, 156.7 mmol) was added to give a suspension. H$_2$O (33 mL) was added. The reaction mixture was heated at 60° C. for 13 hours and was allowed to cool to room temperature. The reaction solution was acidified to pH 2 using 1N KHSO$_4$ (160 mL). The resulting mixture was diluted with EtOAc (250 mL), washed with H$_2$O (2×400 mL) and saturated aqueous NaCl (400 mL), dried over Na$_2$SO$_4$, filtered, evaporated, and dried under vacuum to afford 3.883 g (102%) of compound 7 as a white solid.

The following values were obtained by nuclear magnetic resonance spectroscopy:

$^1$H NMR (CD$_3$OD) δ 7.54 (s, 1H), 7.32 (d, J=7.8 Hz, 1H), 7.28 (dd, J=1.8 Hz, 7.8 Hz, 1H), 3.81 (m, 1H), 3.72 (septet, J=6.9 Hz, 1H), 2.81 (d, J=3.7 Hz, 2H), 2.55–2.68 (m, 2H), 1.6–1.70 (m, 4H), 1.44 (s, 9H), 1.22 (d, J=6.9 Hz, 6H).

Alternative Route for Synthesis of Compound 7

Preparation of Ethyl 2-isopropyl-5-(formylmethyl)benzoate (Compound 2)

In a 15 L four necked-flask equipped with a mechanical stirrer, a digital thermometer and an addition funnel in dark (apparatus was covered with aluminum foil), compound 1 (700 g, 2.82 mol) was dissolved in CH$_3$CN (7 L) and H$_2$O (385 mL). A flask was immersed in a water bath at 40° C. To this stirring solution, 385 mL of 55% HI (2.82 mol) was added dropwise over 20 minutes at 11–25.8° C., and the mixture was stirred for 1 hour at 25.8–30° C. HPLC was performed on the reaction mixture (Method 1; a small amount of reaction mixture was diluted with mobile phase and injected) and revealed no remaining starting material. The reaction mixture was transferred to a 40 L reactor, diluted with water (6.3 L) and extracted with EtOAc (8.4 L). The organic layer was separated, washed with 2.5% Na$_2$S$_2$O$_3$, H$_2$O (6.3 L), 5% NaHCO$_3$ (4.2 L), 10% brine (6.3 L×2) dried over MgSO$_4$ and the solvent was removed under reduced pressure at 40 to obtain compound 2 as a brown oil. (637.6 g, 97%). HPLC purity was 77%, (Method 1).

Preparation of Methyl 2-isopropyl-5-{(E,Z)-3-[(4S)-2-oxo-1,3-thiazolan-4-yl]-2-propenyl}benzoate (Compounds 3a,3b)

In a 15 L four-necked flask equipped with a vacuum sealed mechanical stirrer, a digital thermometer and septums, the indicated phosphonium salt RO12M (722 g, 1.43 mol) was suspended in THF (7220 mL) at −62° C. To this stirring suspension, n-BuLi (2.5M in hexane, 1116 mL, 2.79 mol) was added dropwise via cannula over 40 min at −62~−40° C. Then the mixture was slowly warmed to −33° C. over 42 minutes and added a solution of compound 2 (318.7 g, 1.36 mol) in THF (1600 mL) was added dropwise over 50 minutes at −33~−30° C. The mixture was poured into cold 1N-HCl (8.8 L) in a 40 L reactor and extracted with 4.4 L of toluene. The organic layer was separated, washed with 6N-HCl (4.4 L), saturated NaCl (8.8 L×4), dried over $MgSO_4$ and concentrated under reduced pressure at 50° C. to give 481.1 g of compound 3a,3b as a brown oil. The yield was calculated to be 70% based on weight-based HPLC assay. HPLC purity was 40% (Method 1).

Preparation of Methyl-2-isopropyl-5-{(E,Z)-3-[(4S)-2-oxo-1,3-thiazolan-4-yl]-2-propenyl}benzoicacid (Compound 22)

To a stirring solution of crude compound 3a,3b (401.4 g, 1.2 mol) in 840 mL of dimethyl sulfoxide and 840 mL of acetonitrile was added 1204 mL of 5 N sodium hydroxide solution (6.02 mol, 5 eq) at room temperature and the resulting mixture was heated at 40° C. for 4 hours. After 4 hours, HPLC (Method 2, a small amount of reaction mixture was diluted with mobile phase and injected) showed that the reaction was complete. The reaction mixture was diluted with 1600 mL of t-butyl methyl ether and 2150 mL of water. The aqueous layer was separated and washed with 1600 mL of t-butyl methyl ether. The aqueous layer was acidified with 1200 mL of 6 N hydrochloric acid and extracted with 2000 mL of t-butyl methyl ether. The organic layer was separated, washed with 1200 mL of water, 1200 mL of 5% sodium chloride solution, dried over 20 g of anhydrous magnesium sulfate, filtered, and concentrated under reduced pressure to give 252 g of Compound 22 as a red brown oil. HPLC purity was 81.1% (Method 2).

Preparation of Compound 22 Dicyclohexylamine Salt (Compound 23)

In a 10 L four-necked flask equipped with a mechanical stirrer, a digital thermometer and addition funnel, Compound 22 (237 g, 0.78 mol) was dissolved in acetone (4744 mL) and the mixture was heated at 40° C. with an oil bath. To this stirring solution, dicyclohexylamine (157 mL) was added dropwise over 30 minutes at 40–48° C. The oil bath was removed and the mixture was cooled to 13° C. with an ice bath. The mixture was passed through Celite to remove insoluble sticky material. The filtrate was concentrated under reduced pressure at 40° C. to afford crude dicyclohexylamine salt as yellow solids. The solids were suspended in 2 L of AcO"Pr and stirred for 30 minutes at room temperature, then diluted with 2 L of heptane. After stirring for an additional 10 minutes at room temperature, the precipitates were collected by filtration, washed with AcO"Pr (300 mL) and air—dried overnight to give 294.6 g of dicyclohexylamine salt (compound 23) as pale yellow solid.

Preparation of Compound 22 Dicyclohexylamine Hydrochloride Salt (Compound 24)

In a 5 L four-necked flask equipped with a mechanical stirrer, a digital thermometer, compound 23 (294 g) was suspended in 2.5 L of AcOEt, and 777 mL of 1 N HCl was added. The mixture was stirred for 1 hour at room temperature, and the resulting insoluble dicyclohexylamine HCl salt was removed by filtration. The filtrate was transferred to a 5 L separatory funnel. The organic layer was separated, washed with 10% brine (2.5 L), dried over $MgSO_4$ and concentrated under reduced pressure at 40° C. to afford 165.2 g of compound 24 as a brown amorphous solid (86% from compound 3a,3b). HPLC purity 91% (Method 2).

Preparation of 2-Isopropyl 5-{3-[(4S)-2-oxo-1,3-thiazolan-4-yl]propyl}benzoic Acid (Compound 25)

In a 38 L autoclave, a mixture of 608.4 g (1.99 mol) of compound 24 and 300 g of 10% palladium-carbon (50% wet) in 12 L of methanol was hydrogenated at 70 $kg/cm^2$ of hydrogen at 50° C. for 5 hours. After the 5 hours, HPLC analysis (Method 3) showed 5.4% of the starting material remaining. The reaction was continued overnight at 70 $kg/cm^2$ of hydrogen at room temperature. After confirming that the reaction was complete, the mixture was filtered through Celite (900 g) and washed with methanol (3 L). The filtrate was divided into three portions and concentrated under reduced pressure at 50° C. to afford pale yellow crystals (540.1 g). The crystals were suspended in 1.5 L of AcO"Pr. After stirring at room temperature for 2 hours, the crystals were filtered, washed with AcO"Pr (300 mL) and dried at 40° C. for 4 hours to give 308 g of compound 25 as pale yellow crystals (50.3% yield). H PLC purity: 98.3% (Method 3).

The filtrate was concentrated under reduced pressure to give 164 g of oil, which was treated with 400 mL of AcO"Pr to crystallize remaining compound 25. This second crop was collected by filtration, washed with 100 mL of AcO"Pr and dried to obtain and additional 31.3 g of compound 25 as pale yellow crystals (5.1%). HPLC purity: 90.0% (Method 2).

Preparation of 5-((4S)-4-[(tert-butoxycarbonyl)amino]-5-{[(2S)-2-[(tert-butoxycarbonyl)amino]-5-(3-carboxy-4-isopropylphenyl)pentyl]disulfanyl}pentyl)-2-isopropylbenzoic Acid (Compound 7)

In a 10 L four-necked flask, compound 25 (150 g, 0.488 mol) was dissolved in KOH solution, which was prepared by dissolving 85% KOH (161 g, 2.44 mol, 5 eq) in 5250 mL of water. The solution was stirred under gentle reflux for 17 hours, at which time, HPLC showed a trace amount of starting material and a main peak of amino thiol (Method 4). The reaction mixture was cooled to 11° C. with an ice-bath and to the mixture was added 166 mL of 5% $H_2O_2$ (0.244 mol) over 8 minutes at 9.9–11.3° C. The reaction mixture was stirred at 5.8–7.0° C. for 190 minutes. After confirming consumption of amino thiol by HPLC (Method 4), a solution of 160 g of $(Boc)_2O$ (0.732 mol) in $CH_3CN$ (640 mL) was added at 10.0–12.2° C. The resulting mixture was warmed to 40° C. over 40 minutes and stirred at that temperature for 1 hour, at which time HPLC showed an incomplete reaction (Method 5, 6). An additional solution of $(Boc)_2O$ (8 g) in $CH_3CN$ (32 mL) was added and the mixture was stirred at 34–37° C. for 1 hour and left at 4° C. overnight. The reaction mixture was transferred into a 20 L separatory funnel, diluted with 3 L of ethyl acetate and acidified with 1.4 L of 2 N HCl. The organic layer was separated, washed with 2.5% $Na_2S_2O_3.5H_2O$ (1 L), 5% NaCl (1 L), and concentrated under reduced pressure at 40° C. to afford 266.2 g of crude material as a pale yellow solid. The crude solid (194.6 g*) was dissolved in 2.7 L of $CH_3CN$ at 73.5° C. and cooled to room temperature over 140 minutes to recrystallize. The suspension was then cooled with an ice bath and stirring was continued overnight. The crystals were collected by filtration, washed with $CH_3CN$ (0.5 L), and dried in a drying oven at 40° C. for 23 hours to give 108.6 g of compound 7 as yellowish brown crystals (58.5%**). HPLC purity: 71.7% (Method 6). *Some of the material was accidentally lost. **The crystallization yield was 80%.

Preparation of Methyl(2R)-2-((5 ((4S)-4-((tert-butoxycarbonyl)amino)-5-(((2S)-2-((tert-butoxycarbonyl) amino)-5-(4-isopropyl-3-(((1-R)-1-(methoxycarbonyl)-3-(methylsulfanyl)propyl)carbonyl)phenyl)pentyl)disulfanyl) pentyl)-2-isopropylbenzoyl)amino-4-(methylsulfanyl) Butanoate (Compound 8)

Compound 7 (1.32 g, 3.49 mmol), L-methionine methyl ester hydrochloride (1.72 g, 8.62 mmol), 1 cyclohexyl-3-(2-morpholinoethyl)carbodiimide metho-p-toluenesulfonate (CMC) (4.37 g, 10.32 mmol), and HOBt.$H_2O$ (0.926 g, 6.05 mmol) were combined, and DMF (7 mL) and NMM (N-methyl morpholine)(0.79 mL, 7.19 mmol) were added. The solution was stirred overnight at room temperature. The mixture was diluted with EtOAc (200 mL), washed with $H_2O$ (100 mL), pH 7.2 phosphate buffer (100 mL), HO (100 mL), and saturated aqueous NaCl (100 mL), dried over $Na_2SO_4$, filtered, and concentrated to give an oil. Purification by flash chromatography (eluting with EtOAc/hexanes) furnished 1.13 g (62%) of Compound 8 as a white solid. The following values were obtained by nuclear magnetic resonance spectroscopy:

$^1$H NMR (CDCl$_3$) δ 7.27 (d, J=8.2 Hz, 1H), 7.20 (d, J=7.8 Hz, 1H), 7.13 (s, 1H), 6.49 (br s, 1H), 4.91 (m, 1H), 3.87 (br s, 1H), 3.79 (s, 3H), 3.29 (septet, J=6.9 Hz, 1H), 2.9–3.0 (m, 1H), 2.8–2.9 (m, 1H), 2.61 (m, 4H), 2.25–2.31 (m, 1H), 2.12 (s, 3H), 2.06–2.13 (m, 1H).

Preparation of Compound 9

Compound 8 (3.71 g, 7.06 mmol) was dissolved in $CH_2Cl_2$ (37.0 mL), and $Et_3SiH$ (12.0 mL) was added. TFA (8.6 mL) was added, and the resulting solution was stirred at room temperature for 1 hour. (The reaction progress was monitored by RP HPLC). The solution was concentrated to dryness to afford a yellow oil. Purification by RP HPLC ($H_2O$/MeCN/TFA) gave Compound 9 as a pale yellow oil.

Preparation of Compound 10

Compound 9 (4.93 g, 3.76 mmol) was dissolved in THF (230 mL). $H_2O$ (78 mL) and $Me_3P$ (12.8 mL, 1 M toluene solution, 12.8 mmol) were added. The resulting solution was stirred at room temperature and monitored by RP HPLC. After about 1 hour, the solution was evaporated to afford a pale yellow oil. Purification by RP HPLC ($H_2O$/$CH_3CN$/TFA) afforded fractions containing the desired compound. These combined fractions were concentrated to a volume of about 200 mL, and 20% aqueous HCl (1.5 mL, 8.25 mmol) was added. The volume was diluted to 1.5 L using sterile $H_2O$, and the solution was filtered (0.45 micron filter). The filtrate was lyophilized to afford 2.853 g (82%) of Compound 10 as a white solid. The following values were obtained by nuclear magnetic resonance spectroscopy:

$^1$H NMR (CD$_3$OD) δ 7.33 (d, 7.8 Hz, 1H), 7.28 (dd, J=2.1 Hz, 8.0 Hz, 1H), 7.15 (d, J=1.8 Hz, 1H), 4.76 (q, J=4.6 Hz, 1H), 3.78 (s, 3H), 3.24 (septet, J=7.0 Hz, 1H), 2.87 (dd, J=4.6 Hz, 14.6 Hz, 1H), 2.51–2.72 (m, 5H), 2.16–2.24 (m, 1H), 2.12 (s, 3H), 2.0–2.07 (m, 1H), 1.6–1.8 (m, 6H), 1.24 (q, J=6.9 Hz, 6H).

Preparation of Mesylate Salt of Compound 10, Methyl(2R)-2-((5-((4S)-4-((tert-butoxycarbonyl)amino)-5-(((2S)-2-((tert-butoxycarbonyl)amino)-5-(4-isopropyl-3-((((1R)-1-(methoxycarbonyl)-3-(methylsulfanyl)propyl)carbonyl)phenyl)pentyl)disufanyl)pentyl)-2-isopropylbenzoyl)amino-4-(methylsulfanyl) butanoate In a 2 L four-necked flask equipped with a mechanical stirrer and a digital thermometer, 105 g of compound 7 (0.138 mol) was dissolved in 525 mL of DMF at 20° C., and followed by addition of H-Met-OMe.HCl (57.9 g, 0.290 mol, 1.05 eq., HOBt.H$_2$O (50.7 g, 0.331 mol, 1.2 eq.) and 1-(3-dimethylaminopropyl)-3-ethylcarbodiimide hydrochloride (EDC.HCl) (63.5 g, 0.331 mol, 1.2 eq.) successively. To the resulting cloudy solution at 23° C., 36.4 mL of NMM was added dropwise over 6 minutes. The reaction was gently exothermic and the temperature rose up to 32° C. The solution was stirred at ambient temperature for 2 hours, at which time, a small amount of the reaction mixture was taken and diluted with a mixture of $CH_3CN$:$H_2O$:$HClO_4$ (800:200:1, v/v) and analyzed by HPLC (method 1), which showed an almost complete reaction. After stirring for additional 1 h, the reaction mixture was transferred to a 5 L flask and diluted with 2.1 L of EtOAc and acidified with 5% aqueous KHSO$_4$ solution (1575 mL). The organic layer was separated and washed with 5% NaHCO$_3$ (1575 mL), 5% brine (1575 mL), dried over MgSO$_4$, and concentrated under reduced pressure at 40° C. to give 150.7 g of crude Compound 8 as pale yellow crystals. The crude crystals were dissolved in 450 mL of EtOAc under reflux and diluted with 900 mL of heptane. The oil bath was removed, and the mixture was cooled. Crystals began to precipitate at 36.8° C., and then the mixture was stirred for 1 hour and 10 minutes at room temperature. The crystals were collected by filtration, washed with EtOAc-heptane (1:2, v/v, 200 mL×2) and dried in a drying oven at 40° C. for 4 hours and in a hood for 16 hours to give 108.6 g of compound 8 as white crystals (112.9 g, 77.8%). HPLC purity was 94.9% (Method 7).

Preparation of Methyl (2R)-2-((5-((4S)-4-amino-5-(((2S)-2-amino-5-(4-isopropyl-3-(((1R)-1-(methoxycarbonyl)-3-(methylsulfanyl)propyl)carbonyl)phenyl)pentyl)-disulfanyl)pentyl)-2-isopropylbenzoyl)amino-4-(methylsulfanyl) Butanoate Mesylate (Compound 26)

A 3 L four necked flask equipped with a mechanical stirrer, a digital thermometer and addition funnel was charged with 110 g of compound 8 (0.105 mol), and a solution of TFA (110 mL) in anisole (110 mL) was added at room temperature over 10 minutes. The temperature rose up to 28° C. The resulting dark clear solution was stirred at ambient temperature for 2.5 hours, at which time a small amount of reaction mixture was taken and diluted with 85% aqueous MeOH and analyzed by HPLC (Method 7, 8), which showed there was no remaining starting material, as well as the formation of desired deprotected product along with an undesired tert-butylated by-product, compound 9a. The reaction mixture was diluted with water (550 mL) and neutralized with 60 g of Na$_2$CO$_3$ (0.57 mol). AcOEt (550 mL) was added, and the resulting bilayer mixture was heated at 50° C. for 4 hours. HPLC (Method 2) showed a complete conversion of by-product to desired product. The mixture was transferred to separatory funnel along with 150 mL of AcOEt rinse. The mixture was shaken and separated, and the organic layer was washed with 5% NaHCO$_3$ (500 mL), 10% NaCl (500 mL) and dried over MgSO$_4$. After filtration, the filtrate was concentrated under reduced pressure at 40° C. to obtain 196 g of crude products. This crude material was dissolved in 2 L of acetonitrile in a 5 L four necked flask. To this mixture, while mechanically stirred at room temperature, 14.1 mL of MsOH (0.21 mol) was added dropwise over 3 minutes. After complete addition, a white solid began to precipitate. After stirring for 1.5 hours at room temperature, the solids were collected by filtration, washed with 500 mL of CH$_3$CN and dried at 40° C. in a drying oven for 16.5 hours to obtain 82.7 g of compound 26 (yield 75.8%). HPLC purity was 91.6% (Method 8).

Example 2

Preparation of Compound 15

Preparation of Compound 11

Compound 4b (8.2379 g, 19 mmol) was dissolved in EtOH (200 proof, 250 mL). Cs$_2$CO$_3$ (6.5120 g, 20.02 mmol) was added, and the suspension was stirred at room temperature overnight. Iodine (1.31 g, 10.32-mmol) was added to the homogeneous solution. The mixture was stirred at room temperature until the iodine dissolved (30 minutes). The solution was diluted with EtOAc (1000 mL) and washed with H$_2$O (2×500 mL) and saturated aqueous NaCl (500 mL), dried over Na$_2$SO$_4$, filtered, and concentrated to give a yellow oil. Purification by flash chromatography (EtOAc,/hexanes) furnished 3.6497 g (47%) of 11. The following values were obtained by nuclear magnetic resonance spectroscopy:

¹H NMR(CDCl₃) δ 7.48 (d, j=1.8 Hz, 1H), 7.32 (d, j=7.8 Hz, 1H), 7.25 (d, j=6.9 Hz, 1H), 5.77 (m, 1H), 5.52 (m, 1H), 4.36 (q, J=7.1 Hz, 2H), 4.92 and 4.43 (br s, 1H), 3.63 (septet, J=6.9 Hz, 1H), 3.36 (d, j=6.9 Hz, 2H), 2.8–3.0 (m, 2H), 1.42 (s, 9H), 139 (t, J=7.1 Hz, 3H), 1.23 (d, J=6.9 Hz, 6H).

Preparation of Compound 12

Compound 11 (3.65 g, 8.98 mmol) was dissolved in MeOH (530 mL), and LiOH (6.47 g, 270.2 mmol) was added to give a suspension. H₂O (115 mL) was added. The reaction mixture was heated at 60° C. for 11 hours and was allowed to cool to room temperature. The reaction solution was acidified to pH 2 using 1 N KHSO₄. The resulting mixture was diluted with EtOAc (400 mL), washed with H₂O (2×200 mL) and saturated aqueous NaCl (200 mL), dried over MgSO₄, filtered, evaporated, and dried under vacuum to afford 3.442 g (101%) of compound 12 as a white solid. The following values were obtained by nuclear magnetic resonance spectroscopy:

¹H NMR (CD₃OD) δ 7.53 (s, 1H), 7.33 (d, J=8.1 Hz, 1H), 7.28 (dd, J=1.7 Hz, 8.1 Hz, 1H), 5.76 (m, 1H), 5.48 (m, 1H), 4.94 (br s, 1H), 4.30 (br s, 1H), 3.72 (septet, J=6.8 Hz, 1H), 3.34 (d, J=6.6 Hz, 2H), 3.30–3.32 (m, 1H), 2.83–2.91 (m, 2H), 1.42 (s, 9H), 1.22 (d, J=6.8 Hz, 6H).

Preparation of Compound 13

Compound 7 (3.4 g, 8.98 mmol), L-methionine methyl ester hydrochloride (4.5 g, 22.5 mmol), CMC (11.4408 g, 27.01 mmol), and HOBt.H₂O (2.4511 g, 16.01 mmol) were combined, and DMF (18 mL) and NMM (2.1 mL, 19.1 mmol) were added. The solution was stirred overnight at room temperature. The mixture was diluted with EtOAc (300 mL), washed with H₂O (100 mL), pH 7.2 phosphate buffer (100 mL), H₂O (100 mL), and saturated aqueous NaCl (100 mL), dried over Na₂SO₄, filtered, and concentrated to give an oil. Purification by flash chromatography (eluting with EtOAc/hexanes) furnished 2.6539 g (56%) of compound 13 as a white solid. The following values were obtained by nuclear magnetic resonance spectroscopy:

¹H NMR (CDCl₃) δ 7.28 (d, J=7.8 Hz, 1H), 7.21 (d, J=8.2 Hz, 1H), 7.14 (s, 1H), 6.50 (br s, 1H), 5.74–5.80 (m, 1H), 5.52 (m, 1H), 4.99 and 4.42 (br s, 1H), 4.90 (m, 1H), 3.79 (s, 3H), 3.34 (d, J=6.4, 2H), 3.31 (septet, J=6.9 Hz, 1H), 2.8–3.0 (m, 2.60 (m, 2H), 2.25–2.32 (m, 1H), 2.11 (s, 3H), 2.06–2.13 (m, 1H), 1.41 (s, 9H), 1.24 (t, J=6.9, 6H).

Preparation of Compound 14

Compound 13 (2.94 g, 5.60 mmol) was dissolved in CH₂Cl₂ (28.0 mL), and Et₃SiH (9.0 mL) was added. TFA (6 mL) was added, and the resulting solution was stirred at room temperature for 1 hour. (The reaction progress was monitored by RP HPLC). The solution was concentrated to dryness to afford a yellow oil. Purification by RP HPLC (H₂O/MeCN/TFA) gave compound 14 as a pale yellow oil.

Preparation of Compound 15

Compound 14 (2.37 g, 5.60 mmol) was dissolved in THF (28 mL). H₂O (10 mL) and Me₃P (5.8 mL, 1 M toluene solution, 5.80 mmol) were added. The resulting solution was stirred at room temperature and monitored by RP HPLC. After approximately one hour, the solution was evaporated to afford a pale yellow oil. Purification by RP HPLC (H₂O/CH₃CN/TFA) afforded fractions containing the desired compound. These combined fractions were concentrated to a volume of about 200 mL, and 20% aqueous HCl (1.05 mL, 5.75 mmol) was added. The volume was diluted to 1.3 L using sterile H₂O, and the solution was filtered (0.45 micron filter). The filtrate was lyophilized to afford 1.7014 g (66%) of compound 15 as a white solid. The following values were obtained by nuclear magnetic resonance spectroscopy:

¹H NMR (CD₃OD) δ 8.73 (d, j=7.8, 1H), 7.35 (d, 7.8 Hz, 1H), 7.28 dd, j=1.8 Hz, 8.2 Hz, 1H), 7.16 (d, J=1.8 Hz, 1H), 6.12 (m, 1H), 5.52 (m, 1H), 4.75–4.79 (m, 1H), 3.85 (q, J=6.9 Hz, 1H), 3.78 (s, 3H), 3.47 (d, J=6.9 Hz, 2H), 3.25 (septet, J=69 Hz, 1H), 2.83 (m, 2H), 2.63–2.69 (m, 1H), 2.54–2.60 (m, 1H), 2.16–2.24 (m, 1H), 2.12 (s, 3H), 1.99–2.08 (m, 1H), 1.25 (q, J=6.9 Hz, 6H).

Example 3

Preparation of Compound 21

Preparation of Compound 17

Compound 16 (15.22 g, 113.9 mmol), tBOC-methionine acid (21.60 g, 91.10 mmol), CMC (59.04 g, 13.44 mmol), and HOBt.H₂O (12.27 g, 80.12 mmol) were combined, and DMF (170 mL) and NMM (10 mL, 90.9 mmol) were added. The solution was stirred overnight at room temperature. The mixture was diluted with EtOAc (500 mL), washed with H₂O (250 mL), pH 7.2 phosphate buffer (250 mL), H₂O (250 mL), and saturated aqueous NaCl (250 mL). Back-extracted aqueous washes with EtOAc (3×100 mL) and washed with brine (100 mL). Combined organic layers were dried over MgSO₄, filtered, and concentrated to give an oil. Purification by flash chromatography (eluting with EtOAc/hexanes) furnished 27.77 g (93%) of compound 17 as a solid. The following values were obtained by nuclear magnetic resonance spectroscopy:

¹H NMR (CDCl₃) δ 7.35 (d, J=1.4, 1H), 6.57 (br s, 1H), 6.32 (m, 1H), 6.23 (d, J=2.7 Hz, 1H), 5.18 and 4.26 (br s, 1H), 4.4–4.5 (m, 2H), 2.55–2.6 (m, 1H), 2.48–2.52 (m, 1), 2.1–2.15 (m, 1H), 2.08 (s, 3H), 1.91–2 (m, 1H), 1.43 (s, 9H).

Preparation of Compound 18

Compound 17 (27.77 g, 84.55 mmol) was dissolved in EtOAc (1000 mL). The reaction was cooled to 0° C. using an ice/water bath. HCl gas was bubbled into the solution for approximately 1 hour (reaction was monitored by TLC—Hex/EtOAc). The EtOAc was evaporated to furnish 22.48 g (100%) of compound 18 as a solid.

Preparation of Compound 19

Compound 7 (23.04 g, 60.55 mmol), Compound 18 (24.57 g, 92.44 mmol), EDC (17.37 g, 90.59 mmol), and HOBt.H₂O (9.14 g, 59.68 mmol) were combined, and DMF (60 mL) and NMM (8.0 mL, 72.76 mmol) were added. The solution was stirred overnight at room temperature. The mixture was diluted with EtOAc (1000 mL), washed with H₂O (500 mL), pH 7.2 phosphate buffer (500 mL), H₂O (500 mL), and saturated aqueous NaCl (500 mL), dried over MgSO₄, filtered, and concentrated to give an oil. Purification by flash chromatography (eluting with EtOAc/hexanes) furnished 15.09 g (42%) of compound 19 as a white solid. The following values were obtained by nuclear magnetic resonance spectroscopy:

¹H NMR (CD₃OD) δ 7.42 (t, J=0.9, 1H), 7.27 (d, J=8.2 Hz, 1H), 7.24 (d, J=8.2 Hz, 1H), 7.13 (d, J=1.4 Hz, 1H), 6.58 (d, J=8.7 Hz, 1H), 6.35 (m, 1H), 6.28 (d, J=0.9 Hz, 1H), 4.65–4.68 (m, 1H), 4.44 (d, j=15.6 Hz, 1H), 4.37 (d, j=15.6 Hz, 1H), 3.81 (br s, 1H), 3.16 (septet, J=6.9 Hz, 1H), 2.78–2.86 (m, 2H), 2.5–2.7 (m, 3H), 2.08–2.12 (m, 1H), 2.09 (s, 3H), 1.96–2.06 (m, 1H), 1.44 (s, 9H), 1.21 (dd, J=3.0, 6.6 Hz, 6H).

Preparation of Compound 20

Compound 19 (15.09 g, 25.54 mmol) was dissolved in CH₂Cl₂ (128.0 mL), and Et₃SiH (41 mL) was added. TFA (21 mL) was added, and the resulting solution was stirred at room temperature for 3 hours. (The reaction progress was monitored by RP HPLC). The solution was concentrated to dryness to afford compound 20 as a yellow oil.

Preparation of Compound 21

Compound 20 (12.53 g, 25.54 mmol) was dissolved in THF (75 mL). H$_2$O (26 mL) and Me$_3$P (50 mL, 1 M toluene solution, 50 mmol) were added. The resulting solution was stirred at room temperature and monitored by RP HPLC. After about 1.5 hours, the solution was evaporated to afford a pale yellow oil. Purification by RP HPLC (H$_2$O/CH$_3$CN/TFA) afforded fractions containing the desired compound. These combined fractions were concentrated to a volume of about 1000 mL, and 20% aqueous HCl (3.7 mL, 20.3 mmol) was added. The volume was diluted to 1.9 L using sterile H$_2$O, and the solution was filtered (0.45 micron filter). The filtrate was lyophilized to afford 11.0023 g (82%) of compound 21 as a white solid. The following values were obtained by nuclear magnetic resonance spectroscopy:

$^1$H NMR (CD$_3$OD) δ 8.61 (t, J=5.5, 1H), 8.48 (d, 7.8 Hz, 1H), 7.44 (dd, J=0.9 Hz, 1.8 Hz, 1H), 7.32 (d, J=7.8 Hz, 1H), 7.28 (dd, j=1.8 Hz, 8.2 Hz, 1H), 7.17 (d, J=1.8 Hz, 1H), 6.36 (m, 1H), 6.29 (dd, J=0.9 Hz, 3.2 Hz, 1H), 4.64–4.69 (m, 1H), 4.37–4.5 (m, 2H), 3.18 (septet, J=6.9 Hz, 1H), 2.87 (m, 1H), 2.68–2.72 (m, 3H), 2.51–2.61 (m, 2H), 2.07–2.12 (m, 1H), 2.10 (s, 3H), 1.96–2.06 (m, 1H), 1.65–1.76 (m, 4H), 1.2 (dd, J=4.6 Hz, 6.9 Hz, 6H).

BIOLOGICAL EXAMPLES

Ras proteins mediate the transformation of normal cells to cancer cells in many human cancers. Before becoming membrane associated and fully functional, ras proteins require post-translational addition of a 15 to 20 carbon prenyl group. Compounds which inhibit prenylation will, therefore, inhibit the growth of ras-related cancers.

Compounds of the invention were screened in art-accepted in vitro assays. First, each potential inhibitor compound was shown to inhibit FTase-mediated prenylation (Table 1). Second, each compound was shown to inhibit GGTase 1mediated prenylation (Table 1). Third, each compound was shown to inhibit ras protein post-translational processing in whole cells (Table 2). Clearly, the compounds of the invention inhibit the prenylating activity of FTase, GGTase 1, or in most cases, both enzymes, with different potencies.

Thus, the ability of the compounds of the invention to inhibit protein processing has been demonstrated in two separate in vitro assays. The ability of the compounds of the invention to inhibit ras-related cancer growth has been demonstrated in an in vitro assay and one in vivo experiment. The compounds of the invention are effective inhibitors of ras-related cancers.

Example 4

Inhibition of FTASE and GGTASE Prenylation

The ability of the disclosed inhibitor compounds to inhibit FTase was measured according to a published prenylation assay (Moores et al., J. Biol. Chem. 266:14603 (1991). Partially purified FTase with 3 μM recombinant H-ras and 440 nM [$^3$H] farnesyl pyrophosphate (FPP) (FTase) were used. The inhibitors were diluted in assay buffer, and each assay mixture was incubated 15 minutes at 37° C. Where inhibition of GGTase was measured, partially purified GGTase with 5 μM recombinant H-ras (61 L, CAIL carboxyl-terminus sequence) and 1 μM [$^3$H] geranylgeranyl diphosphate were used.

The IC$_{50}$ (concentration of compound needed to cause 50% inhibition) values are presented in Table 1. Nanomolar concentrations of the indicated compounds were sufficient to inhibit farnesylation of ras proteins in vitro. For screening candidate compounds useful for the treatment of ras-associated tumors, the FTase assay is preferred. The compounds of the invention selectively inhibit FTase. As shown in table 1, the compounds of the invention, and comparative compounds with similar structures, have similar activities in in vitro isoprenylation assays.

TABLE 1

| Structure | IC$_{50}$ [μM] | |
|---|---|---|
| | FTase | GGTase |
| [HS—CH$_2$—CH(NH$_2$·HCl)—CH$_2$—CH=CH—CH$_2$—(aryl-Me)—C(O)NH—CH(COOH)—CH$_2$—CH$_2$—SMe] | 0.001 (4) | 2.17 (5) |
| [HS—CH$_2$—CH(NH$_2$·HCl)—CH$_2$—CH=CH—CH$_2$—(aryl-CH$_2$Me)—C(O)NH—CH(COOH)—CH$_2$—CH$_2$—SMe] | 0.009 | 0.42 |

TABLE 1-continued

| Structure | IC$_{50}$ [μM] | |
|---|---|---|
| | FTase | GGTase |
| (structure: HS-CH2-CH(NH2·HCl)-CH=CH-CH2-[2-iPr-phenyl]-C(O)NH-CH(COOH)-CH2CH2-SMe) | 0.023 (6) | 0.45 (5) |
| (structure: HS-CH2-CH(NH2·HCl)-CH2CH2CH2-[2-iPr-phenyl]-C(O)NH-CH(COOH)-CH2CH2-SMe) | 0.008 (8) | 0.68 (11) |
| (structure: HS-CH2-CH(NH2·HCl)-CH=CH-CH2-[2-Me-phenyl]-C(O)NH-CH(COOMe)-CH2CH2-SMe) | 0.3 | 1.60 |
| (structure: HS-CH2-CH(NH2·HCl)-CH=CH-CH2-[2-Et-phenyl]-C(O)NH-CH(COOMe)-CH2CH2-SMe) | 0.56 | 1.84 |
| (structure: HS-CH2-CH(NH2·HCl)-CH=CH-CH2-[2-iPr-phenyl]-C(O)NH-CH(COOMe)-CH2CH2-SMe) | 0.08 (5) | 3.19 (5) |

TABLE 1-continued

| Structure | IC$_{50}$ [μM] | |
|---|---|---|
| | FTase | GGTase |
| 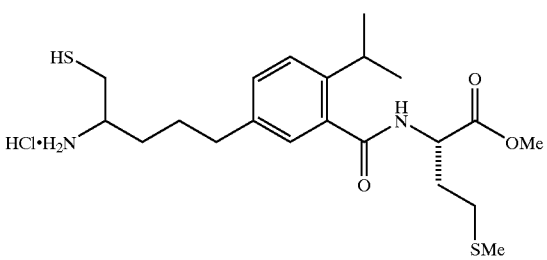 10 | 0.073 (6) | 4.44 (5) |
| 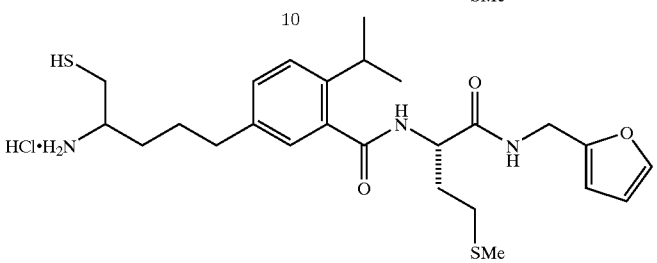 21 | 0.067 (3) | 4.43 (3) |

Example 5

Inhibition of Prenylation in Whole Cells

The ability of compounds of the invention to inhibit H-ras farnesylation and rap1 geranylgeranylation in whole cells was determined. H-ras (61 L) transformed NIH3T3 fibroblasts were generously provided by C. Der, Univ. N. Carolina. These fibroblasts were treated for 24 hours with 50 μM lovastatin (control) or the indicated concentrations of inhibitor. The cells were lysed in 1% NP-40, 5mM Tris-HCl (pH 8.0), 5mM EDTA, 0.1mM N-tosyl-L-phenylalanine chloromethyl ketone, 0.1mM N-tosyl-L-lysine chloromethyl ketone, and 1 mM phenylmethylsulfonyl fluoride. The lysate was centrifuged (15000×g, 5 minutes.) and the supernatant was used as a cell extract. Total protein was separated by SDS-PAGE in 15% acrylamnide gel. After transfer to IMMOBILON P™ membrane (Millipore), the blots were probed with LA069 mouse monoclonal antibody to H-ras (Quality Biotech), or rabbit polyclonal antibody to rap1/Krev (Santa Cruz Biotechnology). All Western blots were developed using ECL chemiluminescent reagents (Amersham).

The IC$_{50}$, values for H-ras are presented in Table 2. Sub-μM concentrations of the indicated compounds are sufficient to inhibit farnesylation of ras proteins in whole cells. In contrast, inhibition of geranylgeranylation of rap1 required compound concentrations in excess of 100 μM (data not shown). Thus, many compounds of the invention inhibit farnesylation more specifically than geranylgeranylation.

When tested for cell based activity, significant differences were observed based on the structures of the compounds (Table 2). First, methyl esters were found to be about 10-fold more potent at inhibiting H-ras post translational processing in vivo, indicating that they permeate living cells to a much greater extent than the corresponding or related acid compounds. When comparing inhibition among methyl esters, the compounds where the phenyl group is substituted with an isopropyl chain were surprisingly and reproducibly more active than compounds with shorter chain substitutions, i.e., ethyl (at least two fold) and methyl (more than 5fold). The same is true for inhibition of anchorage-independent cell growth: the rank of activity of compounds, depending on the substitution of the phenyl ring, is: isopropyl>ethyl>methyl.

TABLE 2

| Structure | IC$_{50}$ [μM] | |
|---|---|---|
| | H-ras | Soft agar |
| 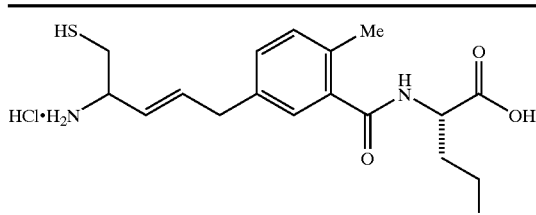 | 4.0 | 9 |

TABLE 2-continued

| Structure | IC$_{50}$ [μM] | |
|---|---|---|
| | H-ras | Soft agar |
| (structure with HS, HCl·H$_2$N, Me, ethyl on ring, amide, CO$_2$H, SMe) | 0.36 | 0.95 |
| (structure with HS, HCl·H$_2$N, isopropyl on ring, amide, CO$_2$H, SMe) | 0.43 (3) | 0.16 (3) |
| (structure with HS, HCl·H$_2$N, saturated chain, isopropyl on ring, amide, CO$_2$H, SMe) | 0.39 (2) | 0.15 (2) |
| (structure with HS, HCl·H$_2$N, Me on ring, amide, OMe ester, SMe) | 0.12 | 0.075 |
| (structure with HS, HCl·H$_2$N, CH$_3$ (ethyl) on ring, amide, OMe ester, SMe) | 0.056 (2) | 0.013 (2) |

TABLE 2-continued

| Structure | IC$_{50}$ [μM] | |
|---|---|---|
| | H-ras | Soft agar |
| Compound 15 (HS-CH$_2$-CH(NH$_2$·HCl)-CH=CH-CH$_2$-[2-isopropyl-5-phenyl]-C(O)NH-CH(CH$_2$CH$_2$SMe)-C(O)OMe) | 0.022 (8) | 0.011 (4) |
| Compound 10 (HS-CH$_2$-CH(NH$_2$·HCl)-CH$_2$CH$_2$CH$_2$-[2-isopropyl-5-phenyl]-C(O)NH-CH(CH$_2$CH$_2$SMe)-C(O)OMe) | 0.028 (7) | 0.019 (2) |
| Compound 21 (HS-CH$_2$-CH(NH$_2$·HCl)-CH$_2$CH$_2$CH$_2$-[2-isopropyl-5-phenyl]-C(O)NH-CH(CH$_2$CH$_2$SMe)-C(O)NH-CH$_2$-(2-furyl)) | 0.20 (2) | 0.30 |

Example 6

Effect of Combination of Compound 10 and Paclitaxel on Anchorage-independent Growth of Tumor Cells in Culture 4×10$^3$ MIA PaCa-2 cells (ATCC CRL1420) were seeded on 24-well culture plates in 0.2 mL of 0.33 Noble agar in 10% fetal calf serum/RPMI1640 medium over 0.4 mL of 0.66% Noble agar in the same culture medium. The top agar layer was overlayed with 0.2 mL of 0.66% Noble agar in culture medium. The upper agar was covered with 0.2 mL of culture medium containing the indicated concentration of paclitaxel and the indicated concentration of compound 10.

The concentrations of paclitaxel used were 0, 0.63, 1.25, 2.5, and 5 nM. The concentrations of compound 10 used were 0, 3.13, 6.25, 12.5, 50, 100, 200, and 400 nM.

At the end of a 17 day incubation, 0.2 mL of 3.3 mg/mL 3-[4,5-dimethylthiazol-2-yl]-2,5-diphenyltetrazolium bromide in phosphate buffered saline was added and incubated for 1 hour. The number of stained colonies was analyzed with an image analyzer computer program. Results are presented in Table 3

TABLE 3

| Compound 10 | Paclitaxel (nM) | | | | |
|---|---|---|---|---|---|
| (nM) | 0 | 0.63 | 1.25 | 2.5 | 5 |
| 0 | 205* | 235 | 234 | 172 | 48 |
| 3.13 | 271 | 255 | 204 | 64 | 8 |
| 6.25 | 210 | 214 | 168 | 36 | 4 |
| 12.5 | 189 | 203 | 148 | 22 | 1 |
| 25 | 161 | 173 | 124 | 16 | 1 |
| 50 | 97 | 119 | 74 | 0 | 0 |
| 100 | 64 | 72 | 26 | 0 | 0 |
| 200 | 23 | 30 | 11 | 0 | 0 |
| 400 | 3 | 6 | 1 | 0 | 0 |

*number of colonies

The data demonstrate that compound 10, at concentrations from 100 to 200 nM, is synergistically tumoricidal with 1.25 nM paclitaxel. Compound 10 at concentrations of 3.13 to 200 nM is synergistic with paclitaxel at concentrations from 2.5 to 5 nM.

Example 7

Synergistic Effect of Compound 10 and Paclitaxel in an in Vivo Tumor Model

5×10$^6$ MIA PaCa-2 cells in Hank's balanced salt solution were injected subcutaneously into the flanks of 6 to 8 week old female nude mice (BALB/c-nu/nu) at day 1. On day 6, the mice were divided into 4 groups (vehicle, paclitaxel 6.25 mg/kg/day, compound 10 25 mg/kg/day, paclitaxel 6.25 mg/kg/day plus compound 10 25 mg/kg/day) when the tumor volume reached about 100 mm$^3$. Compound 10 and paclitaxel were administered intravenously once a day for 5 days from day 6. Tumor volume was measured on the days indicated. Tumor volume was calculated according to the equation: tumor volume (mm$^3$)=(length×width$^2$)/2. The results are shown in FIG. 1, where the bars indicated standard deviation. The n value for the assays is 5.

The data demonstrate that while paclitaxel alone inhibited tumor growth, no tumor regression ever occurred. However, the combination of paclitaxel and compound 10 led to dramatic regression, so that by 20 days after tumor cell implantation, all tumors in all mice had completely regressed, i.e., the mice were tumor free.

What is claimed is:

1. A compound selected from the group consisting of:

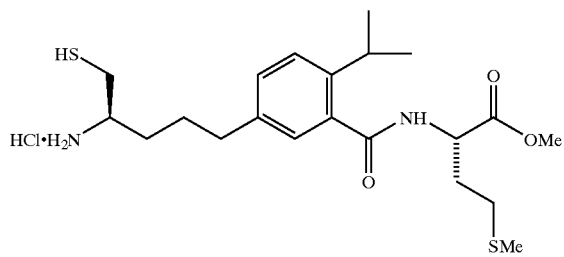

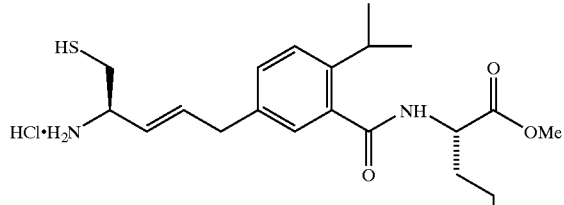

and

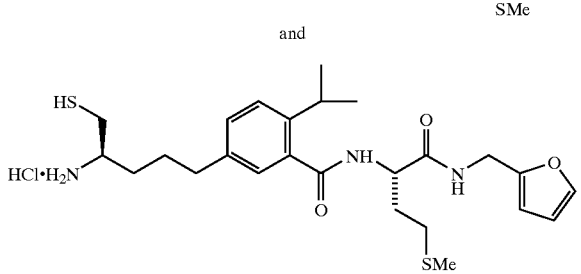

or a pharmaceutically acceptable salt thereof.

2. A pharmaceutical composition comprising a compound selected from the group consisting of

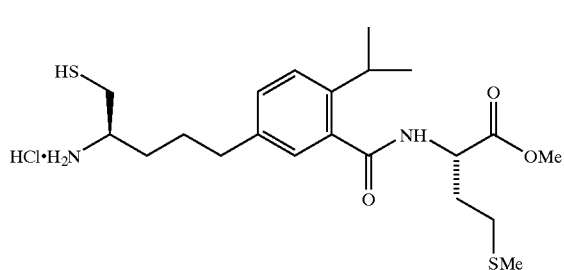

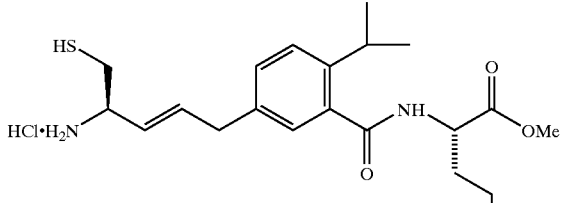

and

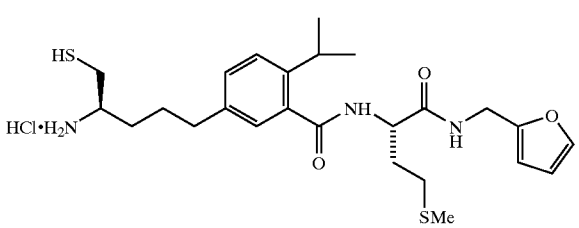

or pharmaceutically acceptable salts thereof; and one or more pharmaceutically acceptable excipients.

3. A method for treating ras-related tumors in a mammal in need of such treatment which comprises administering an effective amount for treating said tumor of a compound selected from the group consisting of

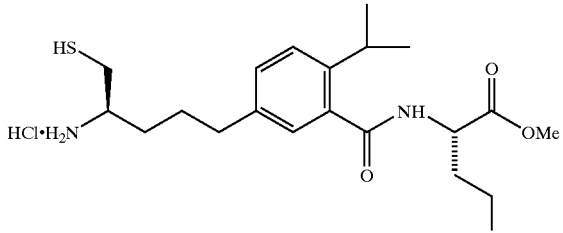

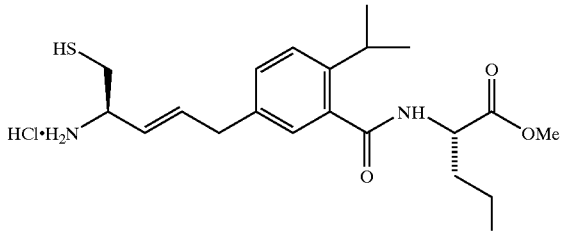

and

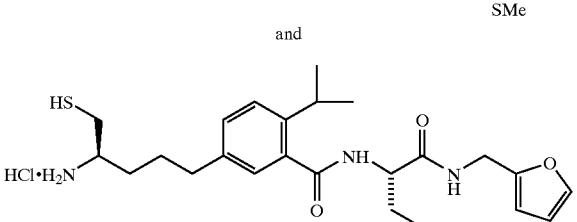

or a pharmaceutically acceptable salt thereof.

4. A method for treating ras-related tumors in a mammal in need of such treatment which comprises administering an effective amount for treating said tumor of a pharmaceutical composition comprising a compound selected from the group consisting of

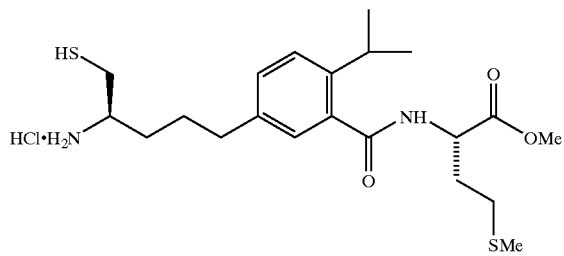

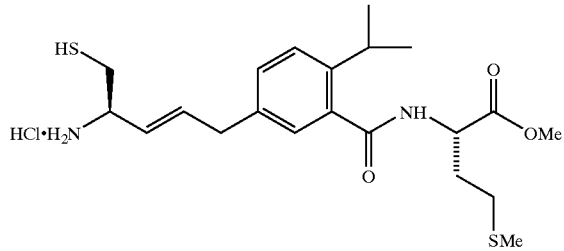

and

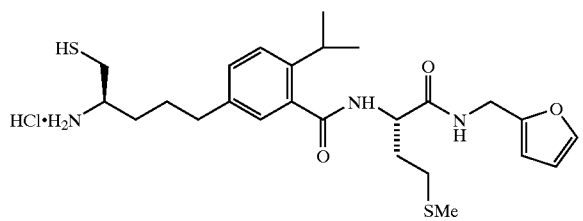

or pharmaceutically acceptable salts thereof; and one or more pharmaceutically acceptable excipients.

5. A method for treating ras-related tumors in a mammal in need of such treatment which comprises administering a first amount of paclitaxel and a second amount of a compound selected from the group consisting of

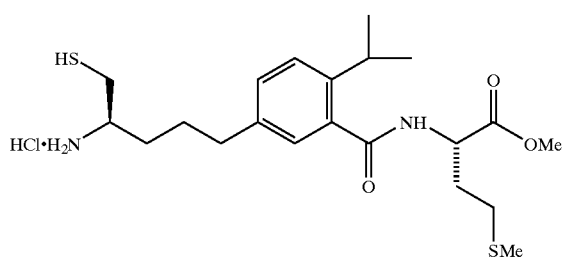

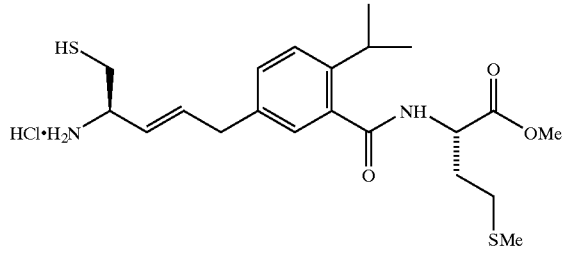

and

-continued

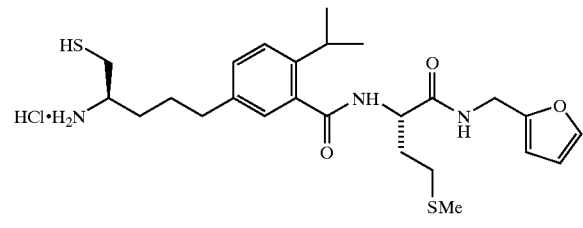

or a pharmaceutically acceptable salt thereof; said first amount of said paclitaxel and said second amount of said compound being effective, in combination, to treat said tumor.

6. A method for treating ras-related tumors in a mammal in need of such treatment which comprises administering a first amount of paclitaxel and a second amount of a pharmaceutical composition comprising a compound selected from the group consisting of

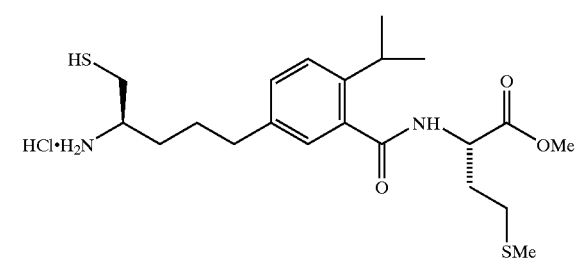

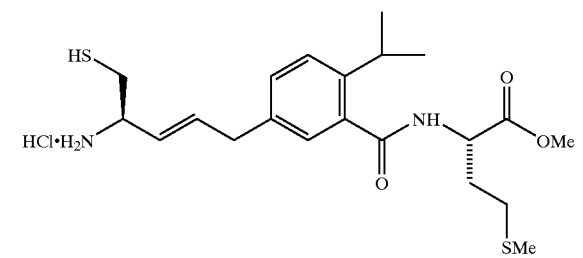

and

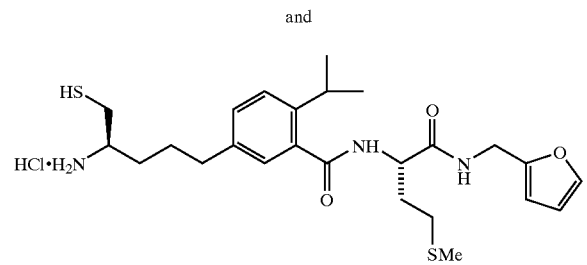

or pharmaceutically acceptable salts thereof; and one or more pharmaceutically acceptable excipients; said first amount of said paclitaxel and said second amount of said pharmaceutical composition being effective, in combination, to treat said tumor.

* * * * *